US011488726B2

(12) United States Patent
Tadi et al.

(10) Patent No.: US 11,488,726 B2
(45) Date of Patent: Nov. 1, 2022

(54) SYSTEM, METHOD AND APPARATUS FOR TREATMENT OF NEGLECT

(71) Applicant: MINDMAZE GROUP SA, Lausanne (CH)

(72) Inventors: Tej Tadi, Lausanne (CH); Daniel Perez Marcos, Lausanne (CH); Roberta Ronchi, Lausanne (CH); Olaf Blanke, Lausanne (CH); Arthur Giroux, Lausanne (CH)

(73) Assignee: MINDMAZE GROUP SA, Lausanne (CH)

( * ) Notice: Subject to any disclaimer, the term of this patent is extended or adjusted under 35 U.S.C. 154(b) by 524 days.

(21) Appl. No.: 15/984,599

(22) Filed: May 21, 2018

(65) Prior Publication Data

US 2018/0336973 A1 Nov. 22, 2018

Related U.S. Application Data

(60) Provisional application No. 62/508,521, filed on May 19, 2017.

(51) Int. Cl.
| | |
|---|---|
| *G16H 80/00* | (2018.01) |
| *G16H 20/30* | (2018.01) |
| *G06F 3/01* | (2006.01) |
| *G06T 19/00* | (2011.01) |
| *A61B 5/00* | (2006.01) |
| *G16H 40/63* | (2018.01) |
| *A61B 5/11* | (2006.01) |
| *G16H 30/40* | (2018.01) |

(Continued)

(52) U.S. Cl.
CPC .......... *G16H 80/00* (2018.01); *A61B 5/0077* (2013.01); *A61B 5/11* (2013.01); *A61B 5/4064* (2013.01); *A61B 5/7267* (2013.01); *G06F 3/015* (2013.01); *G06T 19/003* (2013.01); *G16H 20/30* (2018.01); *G16H 30/40* (2018.01); *G16H 40/63* (2018.01); *G16H 50/20* (2018.01); *A61B 5/0006* (2013.01); *A61B 5/0022* (2013.01); *A61B 5/1116* (2013.01); *A61B 5/1127* (2013.01); *G06T 19/006* (2013.01); *G08B 21/0415* (2013.01)

(58) Field of Classification Search
CPC ........ G16H 80/00; G16H 20/30; G16H 40/63; G16H 30/40; G16H 50/20; A61B 5/0077; A61B 5/7267; A61B 5/11; A61B 5/4064; A61B 5/1127; A61B 5/1116; A61B 5/0006; A61B 5/0022; G06F 3/015; G06F 3/011; G06F 3/014; G06T 19/003; G06T 19/006; G08B 21/0415
USPC .......................................................... 702/19
See application file for complete search history.

(56) References Cited

U.S. PATENT DOCUMENTS

| | | | | |
|---|---|---|---|---|
| 9,949,693 | B2 * | 4/2018 | Sereno | A61B 5/162 |
| 9,978,145 | B2 * | 5/2018 | Gillies | G06K 9/00288 |
| 11,116,441 | B2 * | 9/2021 | Macri | A61B 5/4519 |

(Continued)

OTHER PUBLICATIONS

Assessment of Spatial Neglect with a Virtual Wheelchair Navigation Task; by Laurel J. Buxbaum et al. (Year: 2006).*

*Primary Examiner* — Hirdepal Singh
(74) *Attorney, Agent, or Firm* — Graeser Associates International Inc.; Dvorah Graeser

(57) ABSTRACT

A system, method and apparatus for assessment and optional treatment of spatial attention deficit, such as neglect for example, with computational feedback, based upon tracking the movement of the user.

24 Claims, 37 Drawing Sheets

(51) Int. Cl.
*G16H 50/20* (2018.01)
*G08B 21/04* (2006.01)

(56) References Cited

U.S. PATENT DOCUMENTS

| | | | |
|---|---|---|---|
| 2016/0262608 A1* | 9/2016 | Krueger | G06T 19/006 |
| 2017/0340200 A1* | 11/2017 | Blaha | A61B 3/113 |
| 2018/0036549 A1* | 2/2018 | Reich | A61N 2/004 |
| 2020/0234432 A1* | 7/2020 | Rose | A61H 5/00 |

* cited by examiner

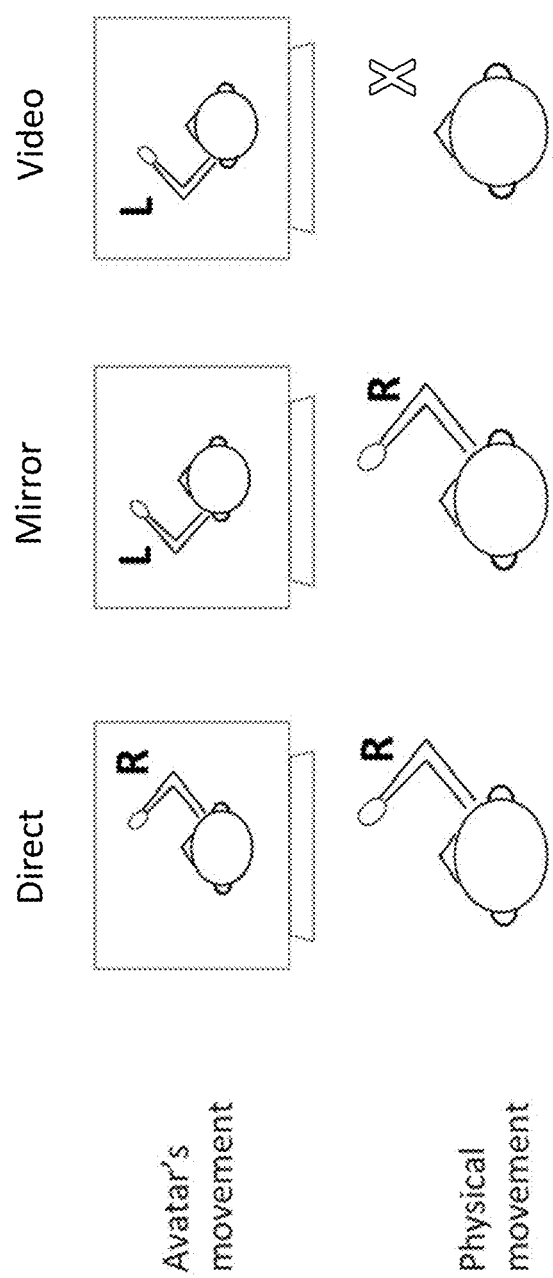

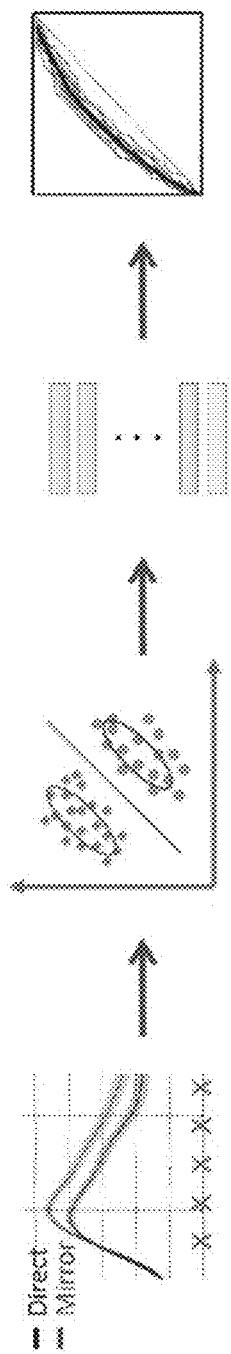

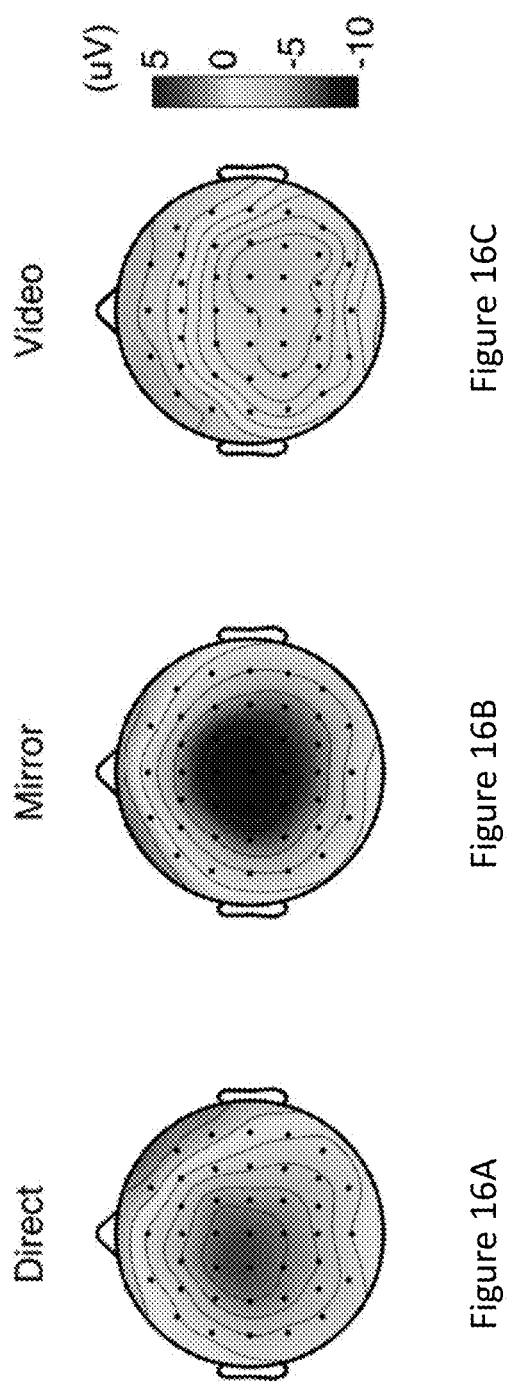

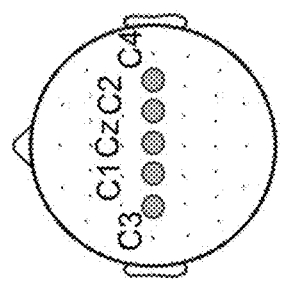
Figure 18A
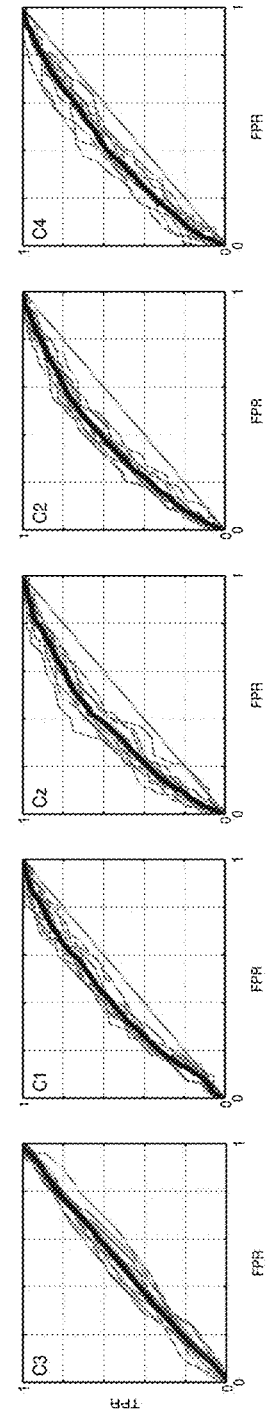
Figure 18B
Figure 18C
Figure 18D
Figure 18E
Figure 18F

SYSTEM, METHOD AND APPARATUS FOR TREATMENT OF NEGLECT

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE INVENTION

The present invention is of a system, method and apparatus for assessment and treatment of neglect, and in particular, to such a system, method and apparatus for assessment and treatment of neglect according to computational feedback, based upon tracking the movement of the user.

BACKGROUND OF THE INVENTION

A stroke is a cerebrovascular accident that happens when the blood flow to a portion of the brain is disrupted, resulting in brain cell death. The consequences can be physical as well as cognitive and can lead to a decrease in movement function and a loss of independence. This disorder is a major cause of long-term physical disabilities and handicaps in Western countries, mostly in the older age range of the population. Thus, as the worldwide population is aging, this disorder is one of the main concerns for the future of health care due to budgetary constraints limiting the intensity and length of the conventional rehabilitative treatment consisting of physical and occupational therapy (C. Bosecker et al. Kinematic robot-based evaluation scales and clinical counterparts to measure upper limb motor performance in patients with chronic stroke. Neurorehabilitation and Neural Repair, 2010).

Many stroke survivors suffer from unilateral spatial neglect (USN). USN is a neuropsychological condition in which, after damage to one hemisphere of the brain is sustained, a deficit in attention to and awareness of one side of space is observed. It is defined by the inability of a person to process and perceive stimuli on one side of the body or environment, where that inability is not due to a lack of sensation. Hemispatial neglect is very commonly contralateral to the damaged hemisphere, but instances of ipsilesional neglect (on the same side as the lesion) have been reported.

The range of neglect can be divided into three categories:
Personal neglect: the patient neglects his own body or personal space.
Peri-personal neglect: The patient does not respond to stimuli that are on one side of his peri-personal space, i.e. within arm's reach. (close-space)
Extra-personal neglect: the patient does not respond to stimuli that are on one side of his extra-personal space, i.e. out of arm's reach. (far-space)

USN is a common and severe consequence of stroke, highly impacting patients' quality of life. Assessing and treating such patients is quite difficult, requiring intensive involvement by a therapist.

An example of a pencil and paper task which is used to assess and attempt to treat neglect is the cancellation task (Wilson, Cockburn, and Halligan in 1987). This test represents a pattern of a random array of verbal and non-verbal visual stimuli. The stimuli are large and small stars, letters, and short words (3-4 letters). The observer asks the patient to say what the patient is observing and then to cross out only the small stars using a colored felt-tip pen. The assessment is limited to the portion of the space of the sheet where the test is provided.

At the end of the task, the observer circles the first star the subject crossed. When the patient leaves the room, the observer fills a sheet indicating:
Left and right omission score: Number of small stars the subject has forgotten to cross in left and right area.
Left and right cancelled item score: Number of other elements cancelled in the right and left area
The number of the first stars crossed (small stars associating number is done by the observer at the beginning of the testing phase)
Perseveration number: Indicate if the patient crosses several times the same elements.

Alternatives to such assessment methods have been sought. For example, Buxbaum et al. ("Assessment of Spatial Neglect with a Virtual Wheelchair Navigation Task", 2006, IEEE) describe a method to assess such neglect by having a patient navigate a virtual wheelchair in a virtual environment. This assessment method was shown correlate well with having the patient navigate the real-world environment in a physical wheelchair. However the method of assessment is very specific to a patient in a wheelchair and to navigational tasks; it cannot be generalized to other AIR, (activities of daily living).

Vaes et al. describe a simpler method, using only an electronic tablet, for assessing peripersonal neglect ("Capturing peripersonal spatial neglect: An electronic method to quantify visuospatial processes", *Behav. Res.*, 25 February 2014). Again this method not generalizable.

Clearly it would be useful to combine assessment with some type of therapeutic measure. Tanaka et al provided digitized standard assessments into a virtual reality (VR) environment with a headset, which was nonetheless limited in its applicability and range of therapeutic effects ("A case study of new assessment and training of unilateral spatial neglect in stroke patients: effect of visual image transformation and visual stimulation by using a head mounted display system (HMD)", *Journal of NeuroEngineering and Rehabilitation*, 2010, 7:20).

Although mirror therapy has been shown to be an effective treatment, its underlying neural mechanisms remain unclear. Furthermore, mirror therapy currently requires intensive participation of a human therapist, limiting access to such therapy and increasing its cost. For example, Tsirlin et al. ("Uses of Virtual Reality for Diagnosis. Rehabilitation and Study of Unilateral Spatial Neglect: Review and Analysis"; *Cyberpsychology& Behavior*, Volume 12, Number 2, 2009) briefly mention the possibility of VR environments being used for mirror therapy. However, the use of VR environments for mirror therapy is currently quite limited, as no robust system is available that can provide a flexible environment for mirror therapy. Merely imitating a physical mirror therapy set up with VR provides only a limited amount of benefit.

This can be achieved by using motion capture technology that interprets the patient's movements and provides multi sensory (vision, audio, touch) feedback to the user about the movement performance. Such enriched VR experiences have been demonstrated to increase patients' motivation (holden, 2005) and facilitate functional recovery by engaging appropriate neural circuits in the motor system (Adamovich, Tunik, & Merians, 2009).

BRIEF SUMMARY OF THE INVENTION

The present invention, in at least some embodiments, is of a system, method and apparatus for assessment and/or treatment of neglect through computational feedback, based upon tracking the movement of the user. Such a system, method and apparatus may be performed with or without the presence of therapist, increasing the therapeutic opportunities for the patient. Optionally any type of neglect may be assessed and/or treated according to a system, method and apparatus as described herein.

As described herein, the term "neglect" includes neglect, spatial attention (including unilateral spatial neglect and extinction, and so forth).

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and the ability to execute one or more instructions may be described as a computer or as a computational device, including but not limited to any type of personal computer (PC), a server, a cellular telephone, a tablet, an IP telephone, a smart phone, a PDA (personal digital assistant), a thin client, a mobile communication device, a smart watch, head mounted display or other wearable that able to communicate externally, a virtual or cloud based processor, or a pager. Any two or more of such devices in communication with each other may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 4A-4C show experimental conditions according to preferred embodiments. The movements of the right arm are mapped onto the avatar's right and left arm for the direct and mirror condition, respectively. In the video condition no physical movement is performed, and pre-recorded reaching movements of the left arm are displayed on the screen.

FIG. 5A illustrates definition of the midline of the body and reversal of the movements of the two arms with respect to the mid-sagittal plane according to preferred embodiments. FIG. 5B illustrates mirroring of position where right-hand movements toward the right correspond to left-hand movements toward the left according to preferred embodiments. FIG. 5C illustrates mirroring of rotation where clockwise right-hand movements correspond to counter-clockwise left-hand movements according to preferred embodiments.

FIGS. 13A-13D show charts illustrating an exemplary classification process for each electrode according to preferred embodiments, including pooling data of subjects and selecting five equally-spaced time-points within 0.92 seconds as feature vector (FIG. 13A); building an LDA classifier (FIG. 13B); performing a 10-fold cross-validation (FIG. 13C); and obtaining the mean ROC curve and the associated AUC (FIG. 13D).

FIGS. 16A-16C show scalp topographic plots of SCPs maximum activity within 0.8 to 1.05 seconds for the three conditions according to preferred embodiments. Stronger and more hemispheric balanced activity is observed in the mirror condition;

FIGS. 18A-18F illustrate exemplary placement of electrodes C3 (AUC=0.51±0.04), C1 (AUC=0.61±0.04), Cz (AUC=0.65±0.04), C2 (AUC=0.65±0.04), and C4 (AUC=0.63±0.04) and corresponding ROC curves according to preferred embodiments.

DESCRIPTION OF AT LEAST SOME EMBODIMENTS

Figure 1A:
FIG. 1A shows a photograph of a user interacting with the MindMotion™ Pro system of MindMaze SA.
Figure 1B:
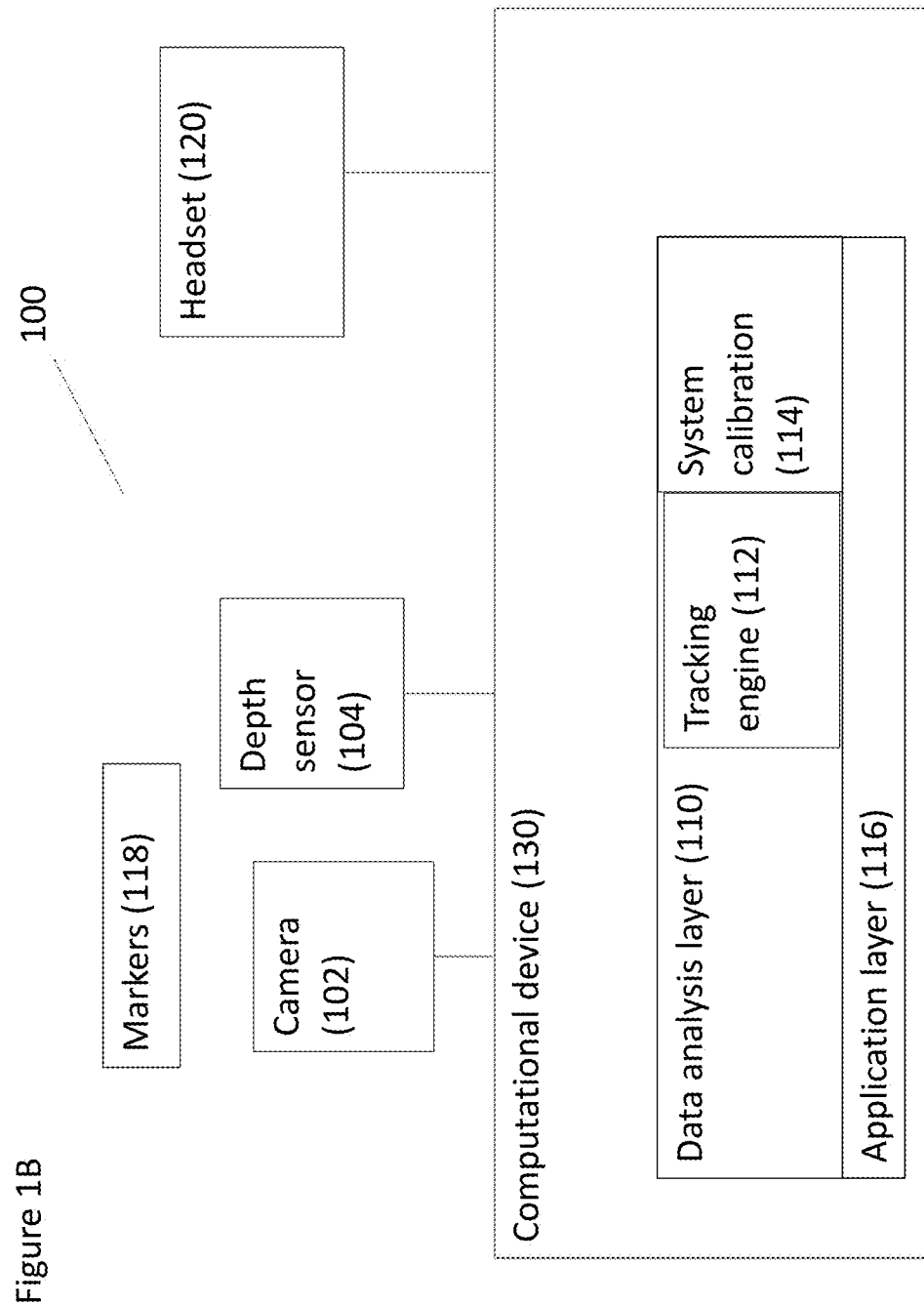
FIG. 1B shows an exemplary system for providing rehabilitation with tracking, which incorporates a number of features of the MindMotion™ Pro system.

FIG. 1A shows a photograph of a user interacting with the MindMotion™ PRO system of MindMaze SA, while FIG. 1B shows an exemplary system for providing rehabilitation with tracking, which incorporates a number of features of the MindMotion™ PRO system. Either or both systems may optionally be used with the methods as described herein.

The MindMotion™ PRO immersive virtual reality (VR) platform provides VR-based exercises for upper-limb neurorehabilitation after brain injuries. The platform is a mobile unit composed for the technical part of a computing unit, a camera with stereo and depth sensors, and embedded 3D image processing system that captures motion by tracking six colored markers positioned on the joints, and two inertial hand sensors that add precision to the orientation of the subject's arm. The colored markers are preferably active markers that emit a signal, such as LED lights for example, and more preferably emit different signals, such as different colored lights. However, optionally no such markers are used in the form of devices attached to the subject, and the markers are instead data points that are detected to determine the location of particular joints in the data obtained.

Optionally no inertial sensors are used; alternatively and optionally, the camera could be replaced by the inertial sensors. Optionally all markers are replaced by the inertial sensors.

Optionally head gaze is provided for interaction input for the task (together with motion tracking of upper limb or alone, as it is the case in the far space).

Positions (3D cartesian coordinates) and orientations (quaternions) of the joints are computer and mapped in real-time onto an avatar following the participant's movement. Motion data are recorded at a suitable sampling frequency, such as 30 Hz for example and without limitation, and are stored in the computation unit for further analysis. Additionally, there are two screens for one for the exercises and one for the monitoring, respectively for the patient and the therapist, and a battery unit.

As described in greater detail below, optionally EEG signals can be measured from the patient (not shown). Optionally also other biosignals could be added including but not limited to ECG (electrocardiogram), EMG (electromyelogram), SCR (Skin Conductance Response), HR (heart rate), HRV (heart rate variability), respiration, as they can be used in potential biofeedback driven approaches for training and/or evaluation of user engagement or stress, among others.

The above system may also optionally include a VR (virtual reality) headset, as described in greater detail below (not shown). The system may also optionally include body motion tracking (not shown). Optionally the system may include multisensory stimulation, e.g. use of haptic and/or force feedback to interact with the virtual environment (not shown).

FIG. 1B shows a system 100 that features a camera 102 and a depth sensor 104.

Optionally camera 102 and depth sensor 104 are combined in a single product, such as the Kinect product of Microsoft, and/or as described with regard to U.S. Pat. No. 8,379,101, for example. The MindMotion™ GO product of MindMaze SA also provides such an implementation through the Kinect product (see for example U.S. Provisional Application No. 62/440,481, filed on Dec. 30, 2016 and owned in common with the present application, which is hereby incorporated by reference as if fully set forth herein). Optionally, camera 102 and depth sensor 104 could be implemented with the LYRA camera of MindMaze SA, for example as implemented in the MindMotion™ PRO product. Preferably camera 102 and depth sensor 104 are integrated together as such integration enables the orientation of camera 102 to be determined in respect of a canonical reference frame.

The sensor data preferably relates to the physical actions of a user (not shown), which are accessible to the sensors. For example, camera 102 may optionally collect video data of one or more movements of the user, while depth sensor 104 may provide data to determine the three-dimensional location of the user in space according to the distance from depth sensor 104. Depth sensor 104 preferably provides TOE (time of flight) data regarding the position of the user; the combination with video data from camera 102 allows a three-dimensional map of the user in the environment to be determined. As described in greater detail below, such a map enables the physical actions of the user to be accurately determined, for example with regard to gestures made by the user.

To assist in the tracking process, optionally one or more markers 118 are placed on the body of the user, Markers 118 optionally feature a characteristic that can be detected by one or more of the sensors. Markers 118 are preferably detectable by camera 102, for example as optical markers. While such optical markers may be passive or active, preferably markers 118 are active markers, for example featuring an active optical marker such as an LED light, a passive marker or some combination thereof. More preferably each of markers 118, or alternatively each pair of markers 118, comprises an LED light of a specific color which is then placed on a specific location of the body of the user. The different colors of the LED lights, placed at a specific location, convey a significant amount of information to the system through camera 102; as described in greater detail below, such information can be used to make the tracking process efficient and accurate. Alternatively, as described above, no such markers 118 are used and instead data points relating to specific joints are detected.

A computational device 130 receives the sensor data from camera 102 and depth sensor 104. Any method steps performed herein may optionally be performed by such a computational device. Also, all modules and interfaces shown herein are assumed to incorporate, or to be operated by, a computational device, even if not shown. Optionally preprocessing is performed on the signal data from the sensors.

The preprocessed signal data from the sensors is then passed to a data analysis layer 110, which preferably performs data analysis on the sensor data for consumption by an application layer 116. By "application" it is optionally meant any type of interaction with a user. Preferably such analysis includes tracking analysis, performed by a tracking engine 112. Tracking engine 112 preferably tracks the position of the user's body and also preferably of one or more body parts of the user, including but not limited to one or more of arms, legs, hands, feet, head and so forth. Tracking engine 112 optionally decomposes physical actions made by the user to a series of gestures. A "gesture" in this case may optionally include an action taken by a plurality of body parts of the user, such as taking a step while swinging an arm, lifting an arm while bending forward, moving both arms and so forth. Such decomposition and gesture recognition could optionally be done separately.

The tracking of the user's body and/or body parts, optionally decomposed to a series of gestures, is then provided to application layer 116, which translates the actions of the user into some type of reaction and/or analyzes these actions to determine one or more action parameters. For example and without limitation, a physical action taken by the user to lift an arm is a gesture which could translate to application layer 116 as lifting a virtual object. Alternatively or additionally, such a physical action could be analyzed by application layer 116 to determine the user's range of motion or ability to perform the action. Application layer 116 could for example provide a game for the user to perform as described herein.

Optionally application layer 116 could create a mirror avatar to provide feedback, which would mirror the user's motions and provide a visual display of such motions.

Data analysis layer 110 also preferably includes a system calibration module 114. As described in greater detail below, system calibration module 114 calibrates the system in regard to the position of the user, in order for the system to be able to track the user effectively. System calibration module 114 may optionally perform calibration of the sensors in regard to the requirements of the operation of application layer 116; however, preferably device abstraction layer 108 performs any sensor specific calibration. Optionally the sensors may be packaged in a device, such as the Kinect, which performs its own sensor specific calibration.

Optionally a headset 120 could be added to the system for a complete VR (virtual reality) experience. A non-limiting example of such a headset is the Oculus Rift. Headset 120 could be connected to computational device 130 either through a wired or wireless connection as described herein. Headset 120 may optionally feature eye tracking, or alternatively eye tracking may optionally be provided through a separate component of the system. Such eye tracking may advantageously be present to determine whether the patient truly accessing certain or all parts of the visual field, or instead is turning his/her head to access different parts of the visual field.

Optionally the system may include multisensory stimulation, e.g. use of haptic and/or force feedback to interact with the virtual environment (not shown). As another example, the system may include headphones, to provide audio feedback or to act as a distraction (not shown).

Figure 2B:
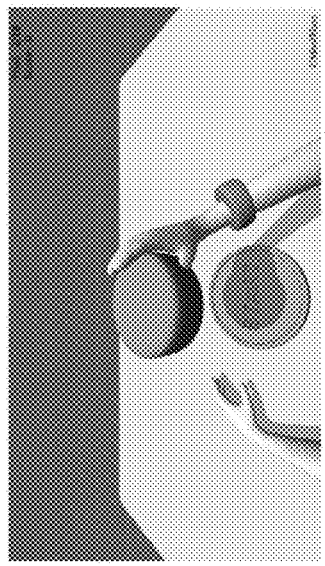
FIGS. 2A-2C show exemplary screenshots of the MindMotion™ Pro system when displaying different interactive rehabilitation games.
Figure 2A:
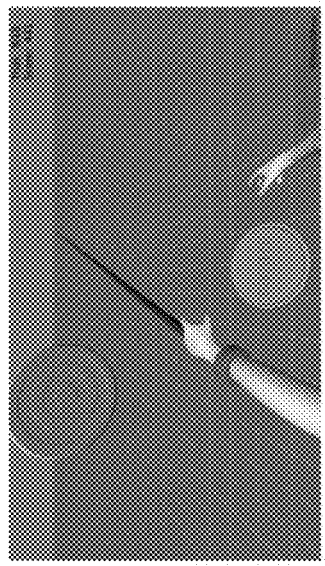
Figure 2C:
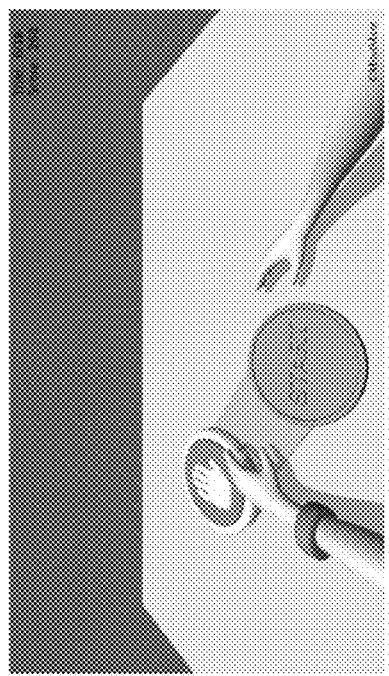

FIGS. 2A-2C show exemplary screenshots of the MindMotion™ Pro system when displaying different interactive rehabilitation games. A game begins, when a start button, or start-pad, appears in the virtual environment, inviting the participant to position his hand on it. Once it is done, a target appears and the participant can start the exercise. The rehabilitation system is composed of four exercises: point, reaching, grasp and fruits champion. The pointing exercise consists in aiming to the center of a target with the arm and stay for a few seconds (FIG. 2A). The grasping game consists of catching an object in the vertical plane (illustrated in FIG. 2B) and drop it in a new location. In the reaching task, the participant has to extend his arm to hit the target (FIG. 2C). Finally, the aim of the fruit champion game is to cut fruits appearing on the screen (not shown). Targets can be located in predefined positions that depend on the difficulty level, the positions during a trial are generated randomly, but are distributed equally across the number of repetition defined.

After each repetition of an exercise, a score appears informing the player about his performance during the task. If the task is not completed within 5 s, a timeout warning appears and the exercise resumes. For example, in the reaching game, the path and wrist-band are blue after the start-pad was hit. Then, if the followed trajectory respects the specified path, the elements mentioned turn green. On the other hand, divergence from the path provoke a change of color to red, inviting the patient to correct his trajectory.

Game events, or triggers, are determined in the MindMotion™ software by the super-position of collision volumes of the hand and the elements of the game (start-pad, path, target). The main events are: contact with the start-pad, contact with the target, mistake feedback on, success/timeout feedback on. The beginning of movement is defined as when the collision volumes of the hand and start-pad do not superimpose anymore, and the end of movement is set when the tip of the participant's fingers reach the target.

Figure 7C:
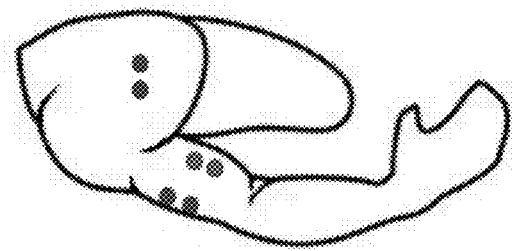
FIG. 7A-7C illustrate exemplary EEG (International extended 10-20 standard), EOG and EMG electrode maps placement, respectively, according to preferred embodiments.
Figure 7B:
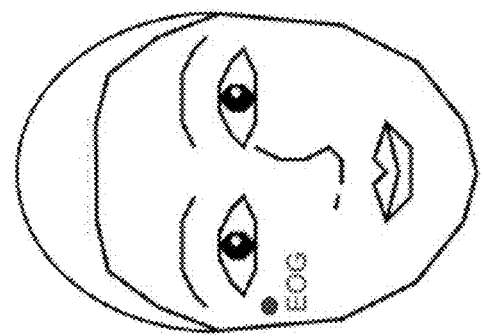
Figure 7A:
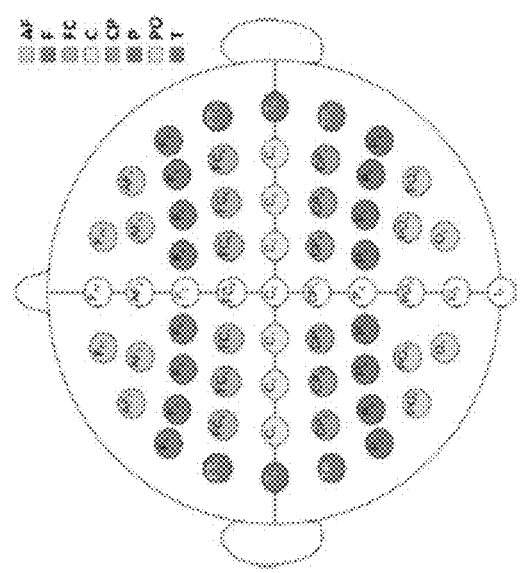

In a preferred embodiment, during the task, EEG, electromyogram (EMG) and electrooculogram (EOG) are recorded. In some preferred embodiments, a Biosemi Inc. ActiveTwo amplifier is used for the recordings with 64 EEG scalp electrodes located according to the international extended 10-20 standard, one EOG electrode and 6 EMG electrodes, as illustrated in FIG. 7. In this embodiment, two EMG electrodes are placed on the biceps brachii muscle of the right arm, two on the triceps brachii muscle, and two on the right pectoralis major muscle, as shown in FIG. 7C. During the data acquisition, the electrode offsets are preferably kept below 20 mV. The signals can be acquired at 2 kHz sampling rate with a low-pass cut-off frequency at 400 Hz.

Motion data is preferably acquired through the motion-capture system at a 30 Hz sampling rate. In some embodiments, only the 3D position of the right hand is analyzed. Further, in some embodiments, the system provides five triggering events for beginning the assessment of the movement of the subject: (1) Target is displayed on the screen (target onset); (2) The participant's hand leaves the start-pad, as detected by the camera (movement onset); (3) The participant performs an error (error feedback); (4) The target is reached successfully (success); and (5) The reward (score or 'time-out') is displayed.

Motion Data Analysis

In preferred embodiments, the 3D coordinates of the right hand are segmented into trials. A trial preferably starts two seconds before the movement onset and ends when the reward appears on the screen. The trajectories of the right hand are visualized and the mean hand trajectory is calculated for each target. For the calculation of the mean trajectory, in order to overcome the fact that each trial can vary in duration the following procedure is performed. The first time-sample of a trial is considered to be t=0 and the last one t=1. Then the data of every trial are fitted in a 5-degree polynomial at equally spaced points depending on the duration of the trial (namely with a step 1/d, where d is the number of samples of each trial). The coefficients of the polynomial are calculated so that they fit the data in the least square sense. In that way, every trial is approximated by a polynomial and normalized in time, so that all trials have equal duration. Data interpolation was then performed; every trial is evaluated in a new timeline from t=0 to t=1 with a time-step 1/dmax, where dmax is the number of samples of the trial with maximum duration. Finally, the mean trajectory of each run was calculated per target from these normalized in time trajectories.

The magnitude of the velocity and acceleration for the right hand (RH) were also computed in cartesian coordinates, per condition and per target, given by the formulas:

$$u = \sqrt{\left(\frac{d}{dt}x_{RH}\right)^2 + \left(\frac{d}{dt}y_{RH}\right)^2 + \left(\frac{d}{dt}z_{RH}\right)^2}$$

$$a = \sqrt{\left(\frac{d^2}{dt^2}x_{RH}\right)^2 + \left(\frac{d^2}{dt^2}y_{RH}\right)^2 + \left(\frac{d^2}{dt^2}z_{RH}\right)^2}$$

For the calculation of the mean velocity and acceleration profiles, the mean across the trials is calculated at every sample-point, namely on as many samples there were available.

Moreover, the reaction time, reach time, number and duration of errors and number of 'time-outs' are calculated and compared (paired t-test). The reaction time is the time interval from the target display until the movement onset. The reach time is the time interval from the target display until the successful reaching of the target.

Example 1—Comparative Efficacy of VR and Tablet Assessment and Rehabilitation

The comparative efficacy of VR (virtual reality) and tablet assessment and rehabilitation, according to a system as described herein, is compared to the efficacy of such assessment and rehabilitation with traditional paper-and-pencil treatment. The comparison is performed with at least 30 neurological patients following a stroke, in the subacute and chronic phase after the stroke; within this group of patients, about 15 patients with spatial neglect will be assessed and then treated according to the tasks.

The VR and tablet-based tasks are administered to the patients a minimum of three times during regular assessment sessions for each patient: (i) before (PRE), (ii) immediately after (POST), and (iii) at one-month follow-up. These assessments are completed during the same sessions where standard paper-and-pencil assessments are administered. Each task and level are completed once, at each time point.

The blocks of paper-, VR- and tablet-based tasks are administered in a counter-balanced order to rule out any training effect. Within each block, they complete all six tasks in a pseudo-random order. The six tasks with tablet were: digitized versions of 6 standard paper-and-pencil assessments for close (i.e., peripersonal) space: star cancellation task, line bisection task (line lengths: 10, 15 and 25 cm), three drawing tasks from a model (Daisy, Butterfly, and House with trees; the latter used for familiarization with the task), and one drawing task from memory (Clock). For the bisection line task, each line (10, 15 and 25 cm) is presented twice in a pseudo-random order. The tablet-based tasks are preferably performed with an electronic computer tablet.

For all the assessments, the patients is sitting comfortably in front of a desk. The tablet is placed centrally with respect to the body midline. For the VR tasks, patients wear a head-mounted display and headphones, as described in greater detail above with regard to FIG. 1B and also in greater detail below with regard Example 3. Example 3 describes some exemplary, non-limiting methods for operating such VR tasks, including without limitation far space and near space VR tasks.

For the tablet-based tasks, the analysis includes at least the following parameters:

| | | |
|---|---|---|
| 1. Star Cancellation | a. | Number of targets cancelled ('accuracy score') and omitted ('omission score') |
| | b. | Number of distracters cancelled and omitted |
| | c. | Number and density of perseveration |
| | d. | Time of exploration |
| | e. | Average marking distance (average distance between two successively cancelled targets) |
| | f. | Average duration and speed of leftward and rightward movements |
| | g. | Number of intersections in the cancellation path |
| | h. | Number of additional drawings |
| | i. | Position of the first mark |
| | j. | Trajectory of pen tip |
| 2. Line Bisection | a. | Mean and std. deviation of the bisection error for each type of line (10, 15, 25 cm) and for all lines |
| | b. | Average time taken for each type of line and for all lines |
| 3. Clock drawing | a. | Number of omissions ('omission score') |
| | b. | Asymmetry index (compares omissions on left side and right side of clock) |
| | c. | Number of perseverations (additional numbers drawn) |
| | d. | Time of exploration |
| | e. | Position of the first mark |
| 4. Daisy, Butterfly & House drawing | a. | Omission score (based on completeness of each element of the drawing) |
| | b. | Asymmetry index (compares omissions on left side and right side) |
| | c. | Area drawn |
| | d. | Laterality index (compares area of left side and right side of drawing) |
| | e. | Number of perseveration (additional elements drawn) |
| | f. | Time taken to perform the drawing |
| | g. | Position of the first mark |

For the VR tasks, the analysis includes at least the following parameters for the far space tasks:
  Omitted Target with their corresponding position and distractors. A target is said omitted if it has not been touched after duration of 2 times the average of reaching time for the trial
  Reaching time for each target: Time required to correctly aiming at a target, i.e. when the light spot changes his color from yellow to blue
  Total time of the task
  Total average marking distance: total average distance between two consecutive cancelled objects (level 1)
  Left and right marking distance: average and standard deviation of distance to go from one object to the following one on the left or the right (level 1)
  Total average and standard deviation of marking time: total average time taken between two consecutive cancelled objects (level 1)
  Left and right marking time: average time to go from one object to the following one on the left or the right (level 1)
  Average and standard deviation of reaching time by column (time required to aim correctly a target in a given column), i.e. the time between the appearance of the animal to the change of light color of spot
  Average and standard deviation of reaching time per side (time required to aim correctly a target for each side), i.e. the time between the appearance of the animal to the change of light color of spot
  Time toward left and right direction (via head orientation data)
  Total omitted targets
  Ratio time: Exploration time on the right (or left)/number of targets cancelled on the right (or left)
  Number and kind of distractors cancelled by mistake
  Exploration time and space as given by hands position
  Optional parameters for the far space tasks (which can also be used for the close or near space task):
  Exploration time by eye gaze (different from current head gaze)

For the VR near (close) space tasks, the analysis includes at least the following parameters:
  Omitted Targets with their corresponding position and distractors. A target is said to be omitted if it has not been touched after a duration of 2× average of reaching time for the trial
  Reaction time for each target
  Time that the participant took to move the hand of 2 cm starting from the appearance of the target
  Reaching time for each target
  Time between the appearance of the target and the moment the target disappears after being touched
  Total time of the exercise
  Average reaction and reaching time by column
  Average reaction and reaching time per side
  Standard deviation of reaction and reaching time per side
  Hand position (via wrist marker position).
  Interpolation of left and right area covered by the hand and calculation of the relative area
  Time toward left and right direction (via head orientation data)
  Total omitted targets
  Ratio time: Exploration time on the right (or left)/number of targets cancelled on the right (or left)

Example 2—Neural Markers for Virtual Environment Mirrored Feedback

This Example relates to neural markers associated with the execution and observation of goal-directed movements under mirrored visual feedback in a virtual environment. Electroencephalography (EEG) data of nine healthy participants (22-35 years) is recorded while they perform a reaching task in virtual reality under three visual feedback modes: a) direct mapping: right arm mapped onto the virtual right arm, b) mirror mapping: right arm mapped onto the virtual left arm and c) passive video control: action observation of pre-recorded movements of the virtual left arm.

Mirror mapping leads to higher negative slow cortical potentials (SCPs) (0.1-1.5 Hz) compared to direct (paired t-test, $p<0.001$) in central electrodes (maximum at Cz). Interestingly, the hemispheric laterality (difference between C3 and C4) is significantly lower in the mirror mapping ($p<0.001$) and performance of single-trial classification (direct versus mirror) is highest for ipsilateral central electrodes (area under curve: 65±–3%), suggesting an activity shift towards the ipsilateral side of the movement. Mere action observation leads to significantly weaker activity compared to direct and mirror mapping ($p<0.001$). The analysis of $\mu$(8-12 Hz) and $\beta$(18-30 Hz) event-related desynchronization shows no significant differences between direct and mirror, thus no conclusive statement is drawn therefrom. Source localization (sLORETA) of $\mu$ and $\beta$ suppression does not show significant differences between the conditions either.

The analysis of SCPs suggests that mirrored visual feedback in a virtual environment can increase the cortical excitability of the hemisphere ipsilateral to the movement. This finding is in line with observations of previous neurophysiological studies on mirror therapy and has important implications in the design of effective rehabilitation procedures using virtual reality.

The virtual environment mirrored feedback can be provided through the previously described MindMotion™ GO system, with the addition of EEG measurements. The system can be operated as described below. Other systems, including systems similar to the system illustrated in FIG. 1B, can also be used.

Figure 3A:
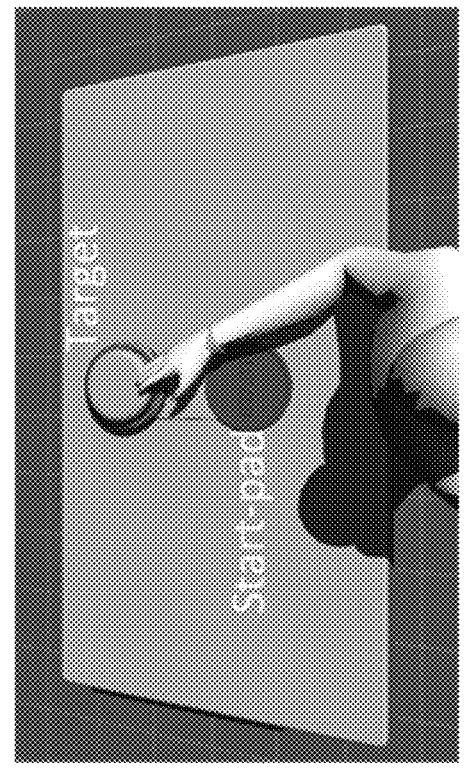
FIG. 3A illustrates an exemplary instruction screen for a mirror feedback task involving reaching in the virtual environment where, starting from a central location, an appearing target should be reached using the avatar's hand.
Figure 3B:
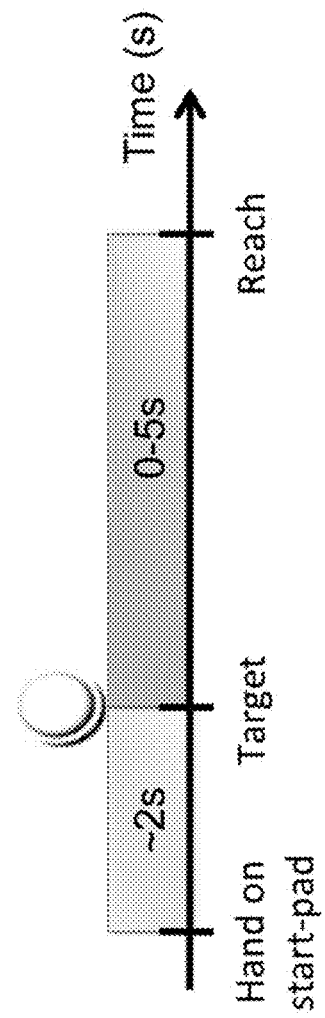
FIG. 3B illustrates a time-line of typical trial of a mirror feedback task according to embodiments of the present invention. Two seconds after the hand placement on the virtual start-pad, a target appears and is reached within five seconds.
Figure 3C:
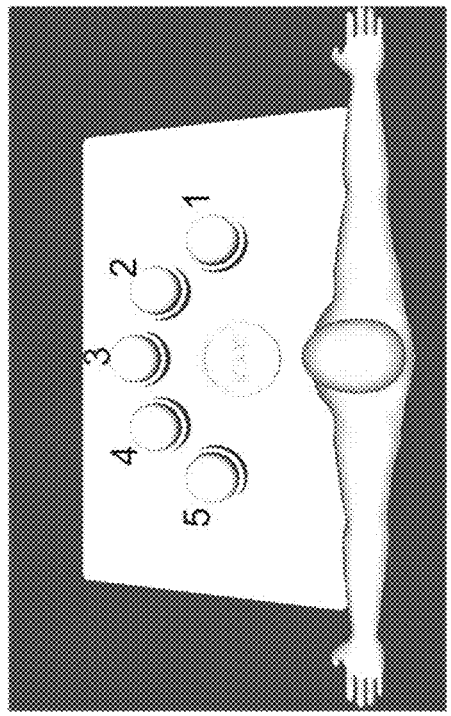
FIG. 3C illustrates an exemplary screen according to preferred embodiments with locations of five possible targets.
Figure 3D:
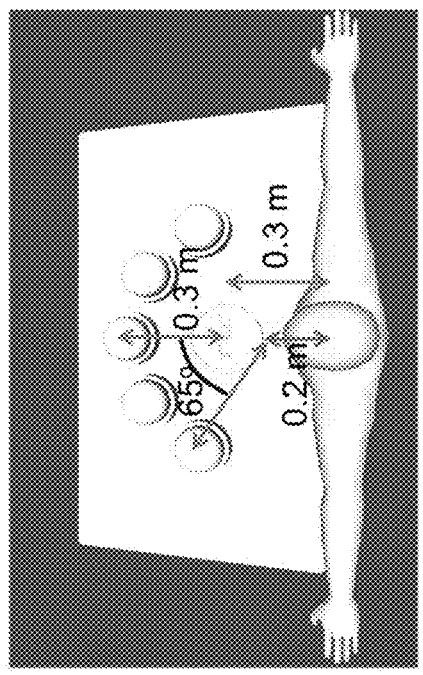
FIG. 3D illustrates an exemplary screen according to preferred embodiments with target distances in the virtual environment.

Approximately two seconds after the participant has placed their right hand on the virtual starting location (start-pad), one of five possible targets is displayed. The participant tries to reach the target using the avatar's fingertip within five seconds. Errors during the movement, for example, divergence from the linear path, are indicated by the color of a band on the avatar's wrist. As an example, the band can display a red color to indicate an error. Other colors can also be used in some embodiments, the end of the trial is accompanied by an obtained score that indicates accuracy. In some embodiments, there is a 'time-out' if the target is not reached within five seconds after its appearance. The locations of the five possible equidistant targets can be seen in FIG. 3C and the distances from the avatar and the start-pad in FIG. 3D. In preferred embodiments, their order of appearance is random across the trials.

Preferably, a participants maintains a roughly predefined posture; legs slightly spread and hand posture similar to that of the virtual hand (i.e., no fist). Additionally, a participant fixates on a marked point at the center of the screen, while performing the task. Preferable, a participant reduces blinks and eye movements as much as possible. A participants preferably waits some time between trials, starting a new one at the participant's own pace. Tasks are made clear to a participant and, preferably, a participant performs a session of five trials where a participant is naïve or not well-acquainted with the device or a trial.

Preferably, the reaching task is performed under three visual feedback modes (FIG. 4): Direct mapping 405, where the right arm was mapped onto the right virtual arm; Mirror mapping 410, where the right arm was mapped onto the left virtual arm; and Passive video control 415, where participants did not perform any movements, but simply watched the avatar per forming pre-recorded reaching movements with the left arm. The terms mapping, condition, and mode are used interchangeably for the remainder of the description. Each condition is preferably performed in three blocks or runs of 50 trials each (total of 150 trials per condition). In some embodiments, the order of the conditions is chosen at random for each participant, while making at the same time sure that the number of combinations is roughly balanced across the participants. Preferably, equal number of trials correspond to each target (10 trials per run, 30 trials per condition).

Figure 5A:
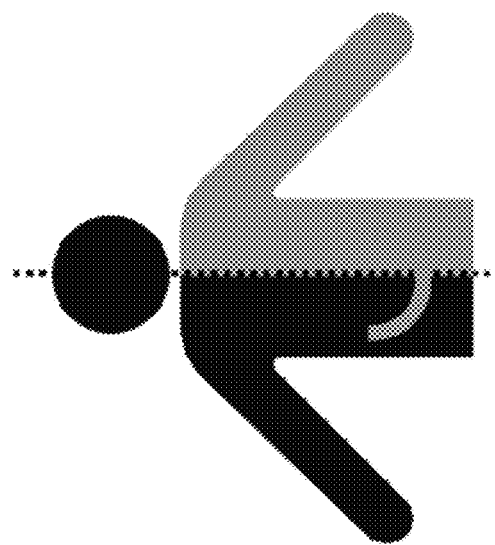
FIGS. 5A-5C illustrate mirror mapping according to preferred embodiments.
Figure 5B:
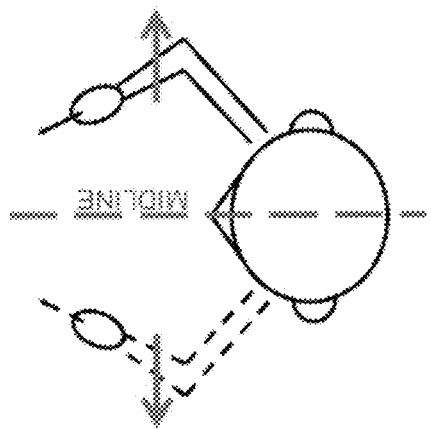
Figure 5C:
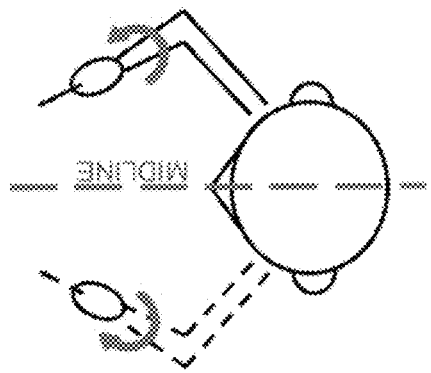

For the mirror condition after obtaining the tracking information from the motion-capture system the midline of the body is defined. The mirroring is then implemented within the MindMotion™ GO software (such as for example application layer 116 of FIG. 1B) by reversing the movements of the two arms with respect to the mid-sagittal plane, both in terms of position and rotation (FIG. 5A). In the mirrored mode, movements of the right arm towards the right direction correspond to movements of the left arm towards the left (FIG. 5B) and clockwise movements of the right correspond to counter-clockwise movements of the left (FIG. 5C). After this manipulation, the new coordinates are rendered to the screen onto the avatar and now the right arm of the participant controls the left arm of the avatar in this mirrored way.

Figure 6A:
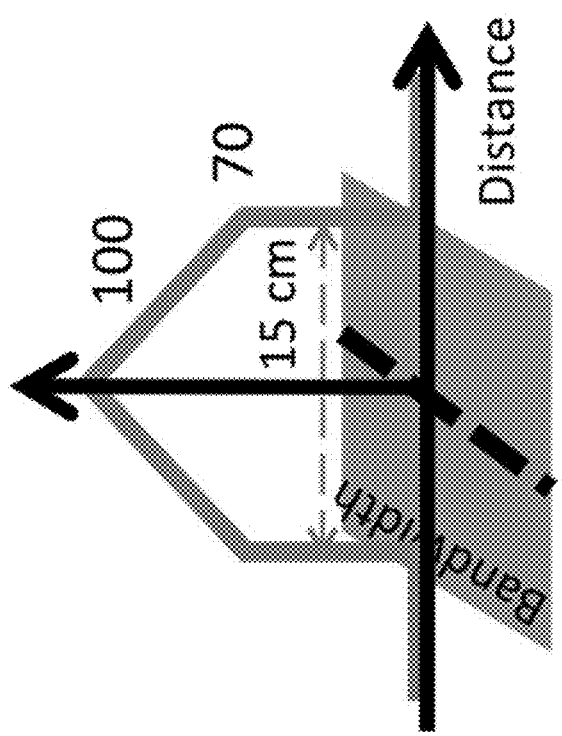
FIG. 6A illustrates a graph of performance metrics (score calculation) computed for the VR reaching tasks according to preferred embodiments. Keeping the virtual hand's fingertip within a path of 15 cm width leads to 100 score, at its edges to 70 and outside of it to 0.
Figure 6B:
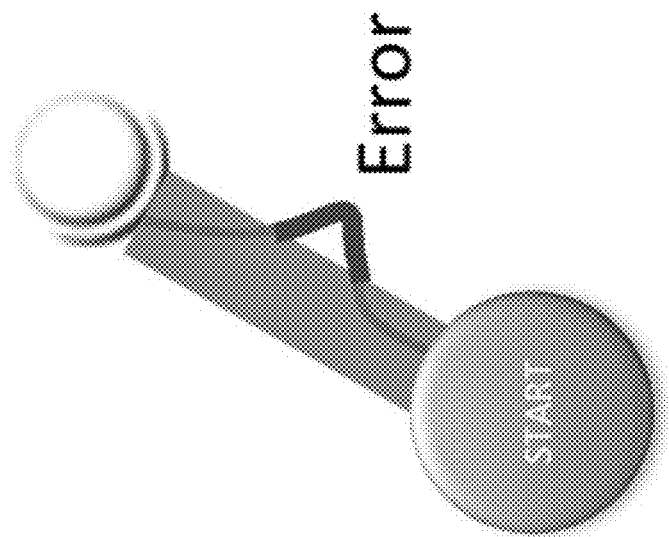
FIG. 6B illustrates a diagram of an exemplary wrong movement path diverging from the straight path and the error portion of the movement path according to preferred embodiments.

FIG. 6A depicts the way the obtained score is calculated in every trial. If the participant moves along a straight pathway, i.e., keeping the avatar's fingertip within a width of 15 cm (marked as green in FIG. 6A), a maximum score of 100 obtained. In a preferred embodiment, the straight pathway range is identified in green. Other colors may be used in some embodiments. Moving at the outer edge of the virtual path results to a score of 70 and moving outside the path counts as 0. The final score of the trial is the average of the scores of each time-sample of the trial. FIG. 6B illustrates the idea of the errors. Moving the avatar's fingertip outside the straight pathway counts as an error. In a preferred embodiment, the band on the avatar's wrist (FIG. 6A) turns into red, providing error feedback to the participant. Other colors may be used in some embodiments.

The study results featured nine participants. The age range of the nine participants included in the analysis was 29±5 years (mean±standard deviation) and seven of them were right-handed. The right hand was always used to perform the task regardless of the handedness, in order to reduce the complexity and the required number of experimental conditions if otherwise. Since the majority of the population is right-handed and to the hemispheric side of a stroke incident is unrelated to the handedness, this choice does not impose any limitation.

During the task EEG, electromyogram (EMG) and electrooculogram (EOG) were recorded. A Biosemi Inc. ActiveTwo amplifier was used for the recordings with 64 EEG scalp electrodes located according to the international extended 10-20 standard, one EOG electrode and 6 EMG electrodes (FIG. 7). Two EMG electrodes were placed on the biceps brachii muscle of the right arm, two on the triceps brachii muscle and two on the right pectoralis major muscle, as shown in FIG. 7C. During the data acquisition it was made sure that the electrode offsets were kept below 20 mV. The signals were acquired at 2 kHz sampling rate with a low-pass cut-off frequency at 400 Hz.

Motion data were acquired through the motion-capture system at a 30 Hz sampling rate. Only the 3D position of the right hand was analyzed. Also, the system provided five triggering events for beginning the assessment of the movement of the subject: (1) Target is displayed on the screen (target onset); (2) The participant's hand leaves the start-pad, as detected by the camera (movement onset); (3) The participant performs an error (error feedback); (4) The target is reached successfully (success); and (5) The reward (score or 'time-out') is displayed.

The data analysis was performed using the Matlab software (Mathworks Inc., USA).

Motion Data Analysis

The 3D coordinates of the right hand were segmented into trials. A trial starts 2 sec before the movement onset and ends when the reward appears on the screen. The trajectories of the right hand were visualized and the mean hand trajectory was calculated for each target. For the calculation of the mean trajectory, in order to overcome the fact that each trial varied in duration the following procedure was performed: The first time-sample of a trial is considered to be t=0 and the last one t=1. Then the data of every trial were fitted in a 5-degree polynomial at equally spaced points depending on the duration of the trial (namely with a step 1/d, where d is the number of samples of each trial). The coefficient of the polynomial were calculated so that they fitted the data in the least square sense (Matlab function: polyfit). In that way every trial was approximated by a polynomial and normalized in time, so that all trials have equal duration. Data interpolation was then performed; every trial was evaluated in a new timeline from t=0 to t=1 with a time-step 1/dmax, where dmax is the number of samples of the trial with maximum duration. Finally, the mean trajectory of each run was calculated per target from these normalized in time trajectories.

The magnitude of the velocity and acceleration for the right hand (RH) were also computed in cartesian coordinates, per condition and per target, given by the formulas:

$$u = \sqrt{\left(\frac{d}{dt}x_{RH}\right)^2 + \left(\frac{d}{dt}y_{RH}\right)^2 + \left(\frac{d}{dt}z_{RH}\right)^2}$$

$$a = \sqrt{\left(\frac{d^2}{dt^2}x_{RH}\right)^2 + \left(\frac{d^2}{dt^2}y_{RH}\right)^2 + \left(\frac{d^2}{dt^2}z_{RH}\right)^2}$$

For the calculation of the mean velocity and acceleration profiles, the mean across the trials is calculated at every sample-point, namely on as many samples there were available.

Moreover, the reaction time, reach time, number and duration of errors and number of 'time-outs' are calculated and compared (paired t-test). The reaction time is the time interval from the target display until the movement onset. The reach time is the time interval from the target display until the successful reaching of the target.

All the aforementioned metrics were calculated run-wise, condition-wise and target-wise both per participant and across all the participants. This served as a means of assessing the difficulty levels of conditions and targets, as well as the evolution across runs/learning effect of the participants, individually and collectively.

Motion Data Analysis Results

Figure 8A:
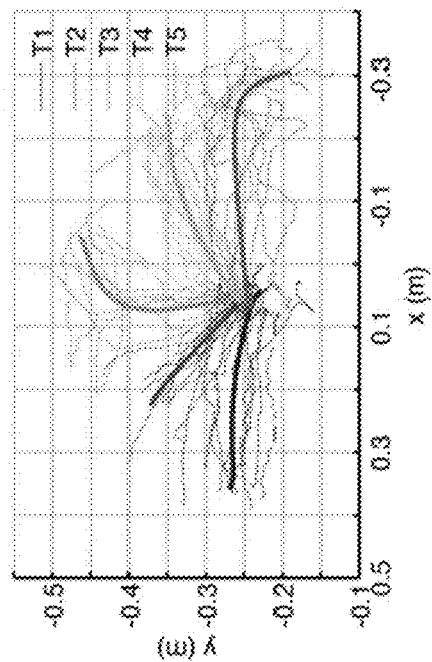
FIGS. 8A-8B show representative direct and mirror hand trajectories for the five targets according to preferred embodiments with higher variability is observed in the mirror mapping.
Figure 8B:
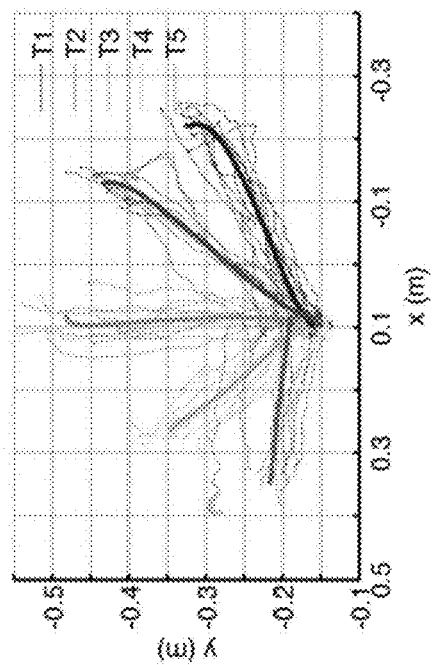

FIG. 8 depicts the hand trajectories of a representative run of the direct and the mirror mapping (50 trials each). The single-trial trajectories are plotted, color-coded for each target and the mean trajectory of each is superimposed. The same target corresponds different direction of the arm in the two conditions. The single-trial hand trajectories are noisier in the mirror mapping, indicating higher variability and error correction.

Figure 9B:
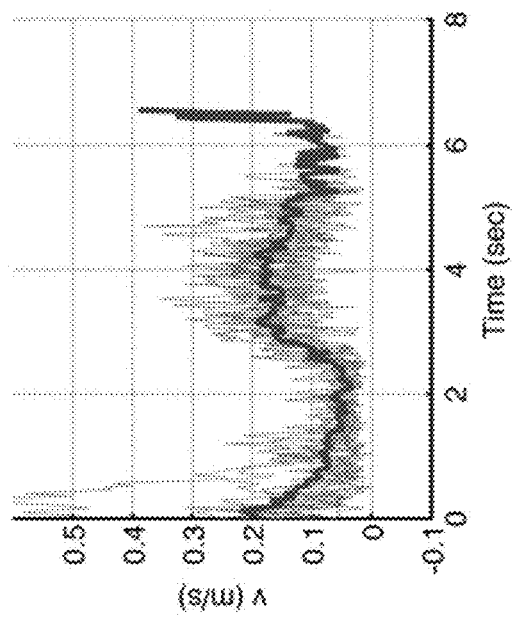
FIGS. 9A-9B show representative direct mapping (target 5) and mirror mapping (target 1) velocity profiles for the same physical target according to preferred embodiments. The obtained velocity profiles are as expected for reaching movements.
Figure 9A:
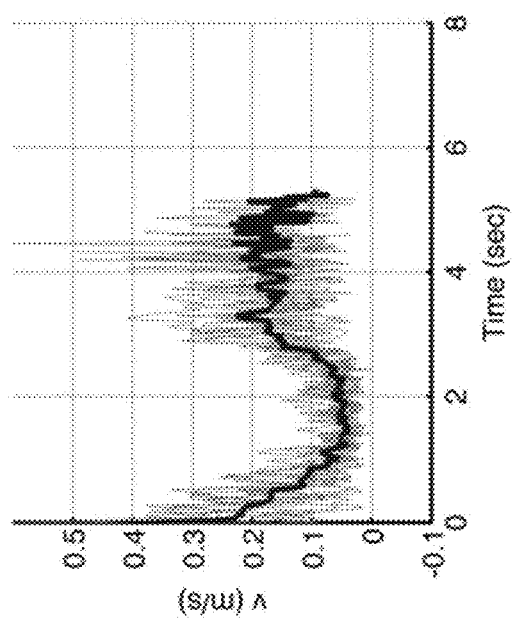

Expected velocity profiles of reaching movements were obtained for both conditions. As a representative illustration, FIG. 9 shows the velocity profiles of one nm for the same physical target during direct and mirror mode (that is T5 for direct and T1 for mirror). The single-trial velocity profiles are plotted in grey and the mean velocity profile superimposed. Further analysis of velocity and acceleration profiles was out of the scope of this project.

Figure 10C:
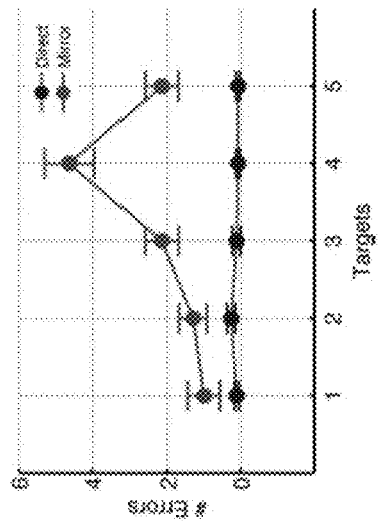
FIGS. 10A-10C show exemplary charts of performance metrics (mean±standard error) across the targets for direct (blue) and mirror condition (red) according to preferred embodiments. Exemplary charts for reach time, accuracy, errors are shown. The performance in the mirror condition is reduced compared to direct and less uniform across the targets.
Figure 10B:
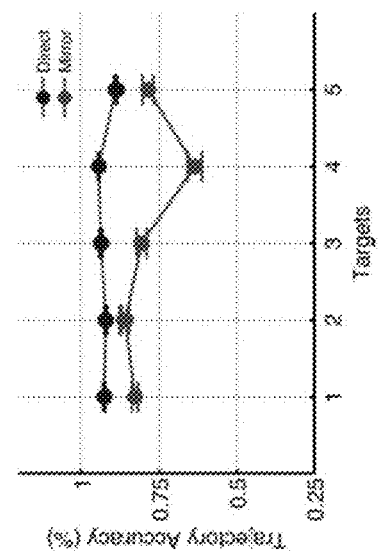
Figure 10A:
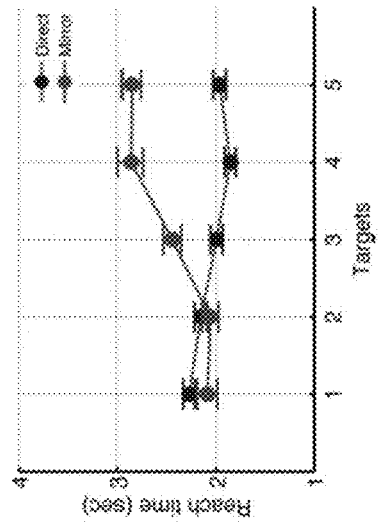

In FIG. 10 three performance metrics are shown per target for the two conditions, averaged across all participants. The mean reach time (FIG. 10A) was longer in the mirror condition compared to the direct (paired t-test, p<0.01) and the mean trajectory accuracy (FIG. 10B) was reduced (paired t-test, p<0.001). Also, in the direct condition there are almost no errors, whereas in the mirror condition the mean number of errors (FIG. 10C) increases significantly (paired t-test, p<0.01). Furthermore, all the three performance criteria appear to be more or less the same across the five targets for the direct condition and relatively more variable within the mirror. Namely, mirror visual feedback led to a less uniform pattern of difficulty level across the five targets. The reaction times were quite similar in the two conditions.

The analysis of performance evaluation shows that the mirror mapping was associated with reduced trajectory accuracy, longer reach time and more errors. Even so, all the performance metrics are still in satisfactory levels and not diminished. The hand trajectories indicate a less standardized, but still consistent profile in the mirror mapping. Moreover, the performance is more variable across the targets within the mirror condition. On the whole, these observations indicate that the task under mirrored visual feedback is more challenging, but still feasible. Behavioral metrics, such as the reaction time and the duration of the trials guided preprocessing steps in the EEG data analysis.

Analysis of Slow Cortical Potentials

Slow Cortical Potentials (SCPs) are scalp-recorded voltage waves with amplitudes up to 50 μV that can last from about half a second up to several seconds (Birbaumer et al., 1990; Garipelli et al., 2013a). Neurophysiologically they are thought to represent excitatory post-synaptic potentials at the apical dendrites of pyramidal neurons with their source in deeper cortical layers close to the neuronal soma (Birbaumer et al., 1990). They are thus thought to reflect the tuning of cortical excitability, subconscious preparation and tissue facilitation (Birbaumer et al., 1990). SCPs have been associated with various behavioral and cognitive aspects, such as voluntary movement and motor preparation (Shibasaki and Hallett, 2006), intention (Birbaumer et al., 1990) and anticipation (Garipelli et al., 2013a). In the domain of voluntary movement, a steep negative deflection around 400 msec before movement onset has been reported, called late bereischaftspotential or readiness potential. This component occurs in the primary motor cortex contralaterally to the movement and to the lateral premotor cortex in a quite precise somatotopical manner, namely over the contralateral central area (C1 or C2 electrodes of the international 10 20 standard) for right hand movement and at the midline (Cz electrode) for foot movements (Shibasaki and Hallett, 2006). Below is provided an analysis of SCPs and evidence of differential cortical excitability due to mirrored visual feedback.

Figure 11A:
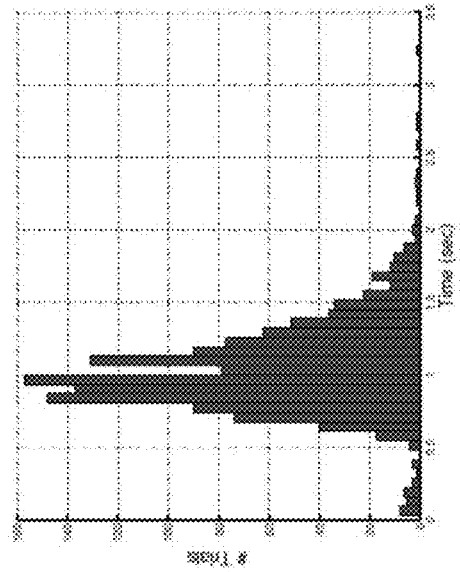
FIGS. 11A-11B show exemplary histograms of the reaction time for a direct condition and a mirror condition according to preferred embodiments.
Figure 11B:
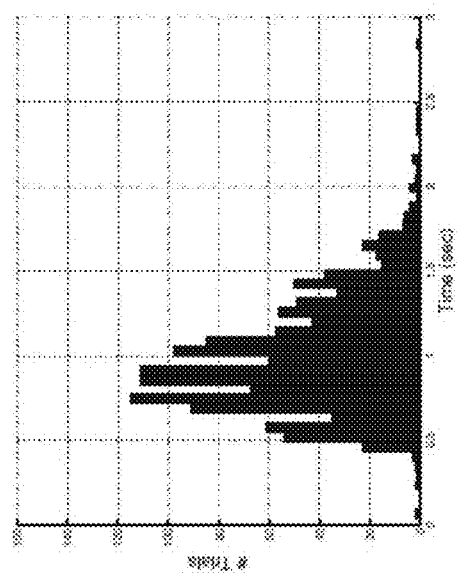
Figure 12A:
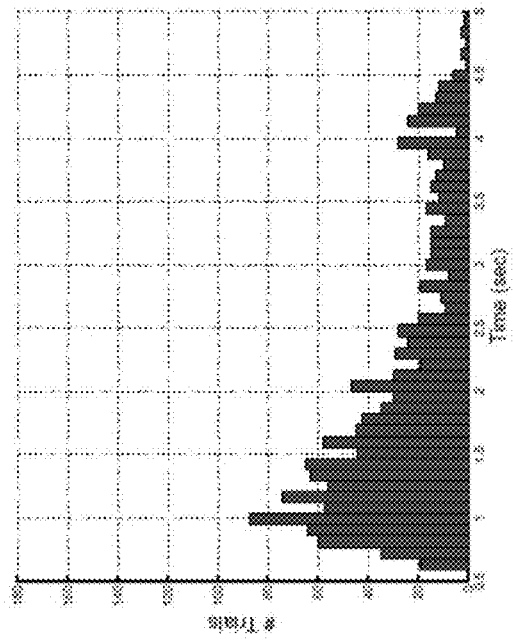
FIGS. 12A-12B show exemplary histograms of trial duration from movement onset until the end for a direct condition and a mirror condition according to preferred embodiments.
Figure 12B:
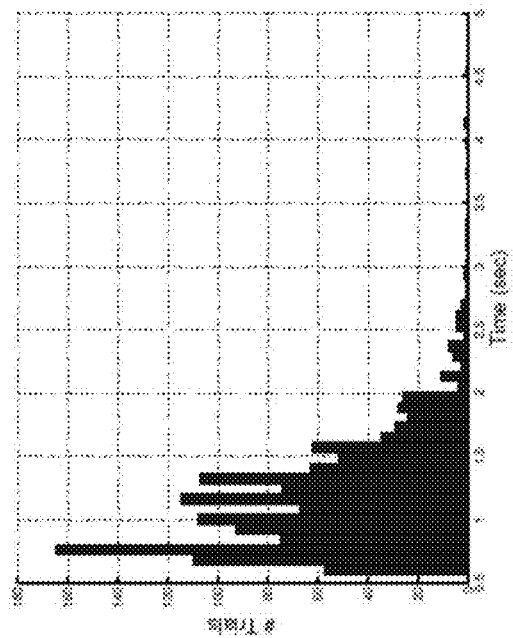
Figure 14A:
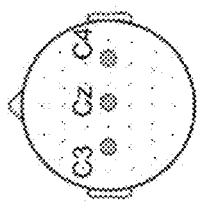
FIGS. 14A-14D show exemplary SCPs waveforms aligned according to Target Display (t=0 sec) for direct (blue), mirror (red) and video (green) conditions with the specified locations of C3, Cz, and C4 electrodes according to preferred embodiments. The shaded area corresponds to the standard error.
Figure 14D:
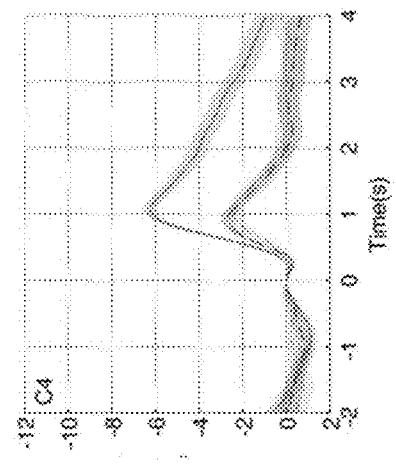
Figure 14C:
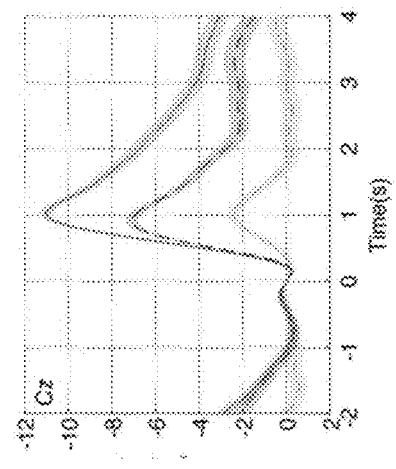
Figure 14B:
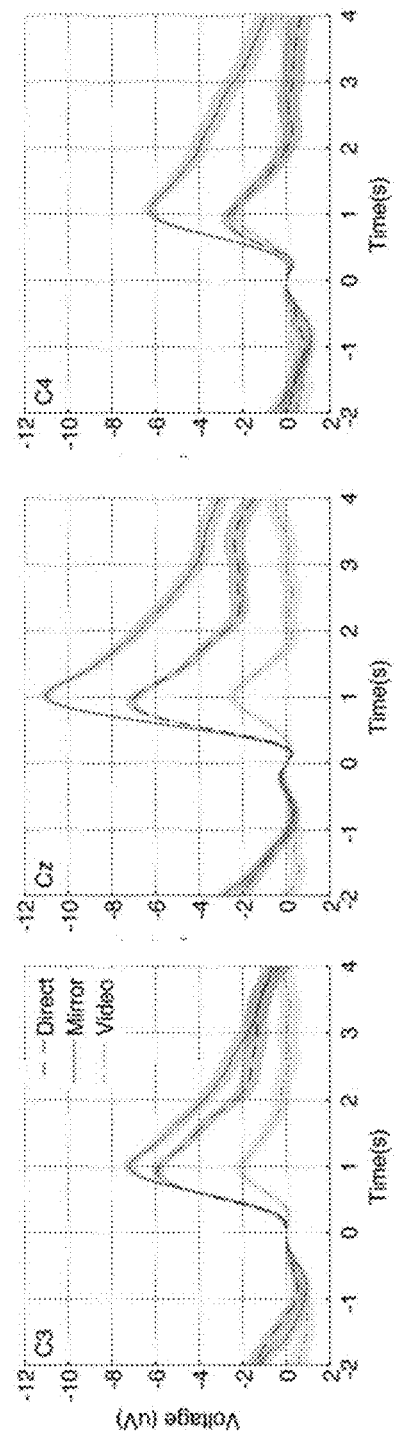
Figure 15A:
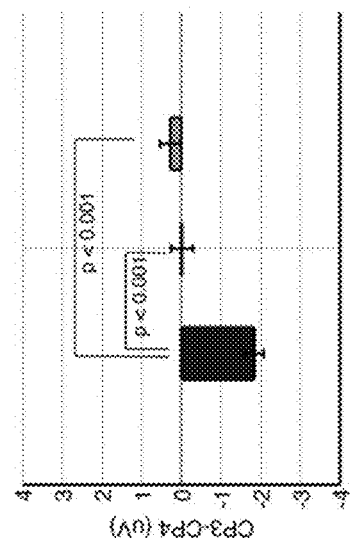
FIGS. 15A-15D show exemplary charts indicating hemispheric laterality with the mean difference between sagittally symmetric channels for direct (blue mirror (red) and video (green) at electrodes C3-C4 (FIG. 15A), CP3-CP4 (FIG. 15B), FC3-FC4 (FIG. 15C), and FC1-FC2 (FIG. 15D) according to preferred embodiments. The error-bars represent the standard error. The p-values of the paired t-tests are also noted.
Figure 15B:
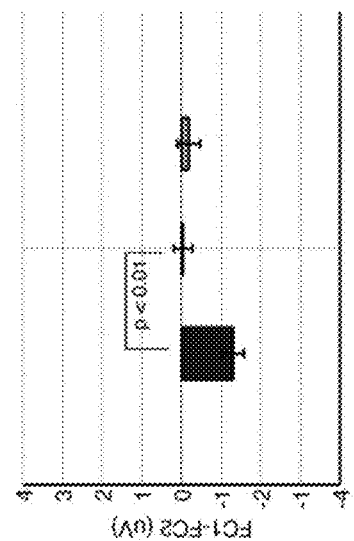
Figure 15C:
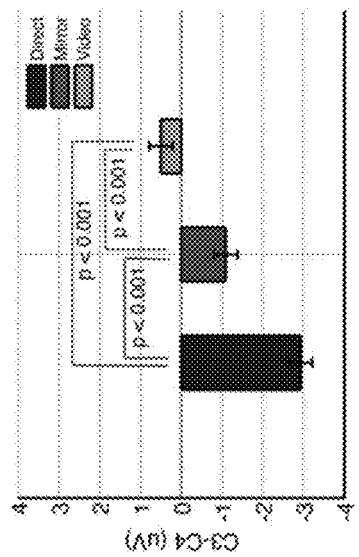
Figure 15D:
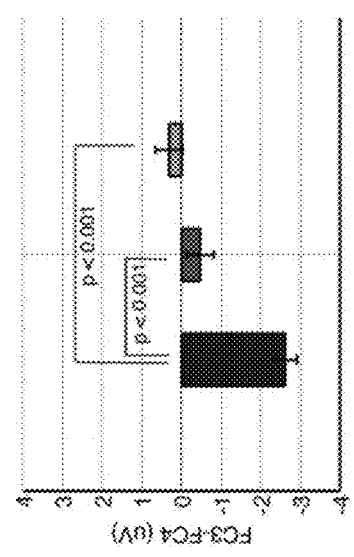

The acquired EEG signals were zero-phase low-pass filtered with a cut-off frequency of 102 Hz and then down-sampled to 256 Hz. The data were then zero-phase band-pass filtered in the frequency range [0.1-1.5] Hz (Butterworth digital filter, order 3) and referenced according to the average activity of T7 and T8 electrodes. Trials were extracted using a [−2 4] sec window with respect to the target onset (t=0 sec). The trials whose maximum voltage EEG Data Analysis The acquired EEG signals were zero-phase low-pass filtered with a cut-off frequency of 102 Hz and then down-sampled to 256 Hz. The data were then zero-phase band-pass filtered in the frequency range [0.1-1.5] Hz (Butterworth digital filter, order 3) and referenced according to the average activity of T7 and T8 electrodes. Trials were extracted using a [−2 4] sec window with respect to the target onset (t=0 sec). The trials whose maximum voltage amplitude exceeded 100 µV (at any electrode) were discarded from the analysis. This voltage threshold was determined through visual inspection of single trials and through a need for a compromise between artifact-free data and number of retained trials. More trials were further rejected according to the reaction time and the duration from the movement onset until the end. The motivation behind this part of trial rejection was to achieve a homogeneity concerning the occurrence of events across the trials, as far as possible. The trials with reaction time less that 0.5 sec and more than 1.7 sec were discarded from the analysis. The choice of these time threshold values was reached through visual inspection of the histogram of the reaction times of direct and mirror conditions (FIG. 11). Using this threshold 93% of direct trials were retained, 94% of mirror and almost all of video. Moreover, the trials whose duration (from the movement onset) exceeded 2 sec for the direct and the video and 4.3 sec for the mirror condition were also excluded from the study (FIG. 12). At this point approximately 95% of the original number of trials were retained for the direct, 97% for the mirror condition and 99% for the video. Since the trials in the mirror condition were fairly longer than the direct, having equal time threshold for the two conditions was not possible, because that would have led to the rejection of a very large number of mirror trials and to an unbalanced dataset. After trial rejection, a total of 909 trials were retained for the direct, 961 for the mirror and 976 for the video condition. Finally the data of each trial were baseline corrected according to the sample at 0 sec (target onset).

The grand average across all participants was computed per condition for each electrode. To compare the conditions, the minimum voltage values at single trial level were extracted within a [0.8 1.05] sec window. This time-window was chosen after visual inspection of the timing of the electrode peak values at the grand-average level. For statistical analysis, repeated measures analysis of variance (ANOVA) and paired t-test with Bonferroni correction were employed. The 23 outer electrodes were not included in the analysis, as more likely to contain artifacts.

In order to study the hemispheric laterality of the SCPs, the differences between the SCPs minimum voltage values were calculated between symmetric pairs of electrodes with respect to the sagittal plane (Kotchoubey et al., 1997; Rockstroh et al., 1990; Touzalin-chretien and Dufour, 2008).

Single-trial classification was performed to test the ability of each electrode to discriminate the SCP data of the two classes direct and mirror, CD and CM respectively. The SCPs were obtained from the raw data similarly to the grandaverage analysis. Additionally common average reference (CAR) followed by weighted average (WAVG), a spatial smoothing filter, were performed. The activity aj at the jth electrode after the application of CAR is given by the formula:

$$a_j^{CAR}(t) = a_j(t) - \frac{1}{N}\sum_i^N a_i(t)$$

where N is the number of electrodes. In WAVG filtering the average activity of neighboring electrodes is added to each electrode, that is:

$$a_j^{WAVG}(t) = a_j(t) + \frac{1}{K}\sum_i^K a_i(t)$$

where i is the index of neighboring electrodes for electrode j (Garipelli et al., 2013a), In our case electrodes within 3.5 cm distance were considered as neighboring ones and the head-size of each individual participant was taken into account for their determination. The application of CAR and WAVG has proven to be suitable for SCPs single-trial classification purposes (Garipelli et al., 2013a).

A diagram of the single-trial classification procedure is depicted in FIG. 13. For each trial the voltage values at five equally spaced time-points within the time-window [0.92] sec were selected as the feature vector (FIG. 13A). This time-window includes the peak values and some subsequent activity. In (Garipelli et al., 2013a) eight features were used for a time-window of 2 sec, based on preliminary analysis. Five features were thus considered sufficient for our case, to describe this 1.1 sec window of SCP data.

The trials of all subjects were pooled together and for each electrode (except for the 23 outer electrodes) a Linear Discriminant Analysis (LDA) classifier was built (FIG. 13B). The underlying assumption of an IDA classifier is that the features vectors of the two classes follow a unimodal Gaussian distribution with same covariance matrix (Duda et al., 2001). According to Bayes theorem the posterior probability of a trial to belong to the direct class CD given a feature vector x is:

$$p(C_D | x) = \frac{p(x | C_D)p(C_D)}{p(x | C_D)p(C_D) + p(x | C_M)p(C_M)}$$

Prior probabilities p(CD)=p(CM)=0.5 were assumed and under the assumption of Gaussian distribution the class-conditional probability is given by the formula:

$$p(x | C_D) = \frac{1}{(2\pi)^{d/2}|\Sigma|^{1/2}} e^{-\frac{1}{2}(x-\mu_D)^T \Sigma^{-1}(x-\mu_D)}$$

where µD is the mean vector for the direct class and Σ is the covariance matrix, computed from the training data of both classes and d is the number of features (d=5). If the posterior probability p(CD|x) is larger than a threshold value θ, the trial with the corresponding feature vector x is assigned to the direct class CD.

Through varying this threshold, we obtain the receiver operator characteristic (ROC) curve. ROC curves depict the true positive rate (TPR) or the sensitivity of the classifier versus the false positive rate (FPR) or the fall-out and serve the evaluation of the classification performance independently of the threshold (Fawcett, 2006).

10-fold cross-validation was performed; data were randomly partitioned into 10 sets (Mat-lab: crossvalind) and at each round 9 folds were used as training data and 1 fold as testing (FIG. 13C). The ROC curve and the associated area under curve (AUC) were obtained for the test data of each fold (FIG. 13D). Finally, the mean ROC curve and the mean AUC across the folds were computed. The standard error of the obtained AUC was calculated according to (Hanley and McNeil, 1982).

The probability of random classification for our case was computed according to (Dunne et al., 2012). The output of a random classifier is independent of the true class label and a conservative approach to estimate random performance is assuming a classifier that always returns the class that occurs more often. Following this approach, the mean probability of random performance across the cross-validation folds was evaluated.

The grand averages across all participants was also computed per target for each condition (for each electrode). For each of the five targets per condition corresponded approximately one fifth of the trials within the condition. Like in the condition-wise grand averages, the minimum voltage values at single trial level within a [0.8 1.05] sec window were used to compare the target-wise grand averages. For statistical analysis, repeated measures 2-way ANOVA with the factors 'conditions' and 'targets' were employed.

The correlation between the target-wise SCP peak negativities and performance metrics was also assessed. To this end, the Pearson correlation coefficient (Matlab: corr) was computed and its statistically significant difference from the hypothesis of no correlation was tested (t-distribution). Correlation was studied both at single-trial and at grand average level (i.e. between target-wise mean values of SCPs peak negativities and performance metrics).

Results—Grandaverages

FIG. 14 shows the SCPs grandaverage waveforms for the electrodes C3, Cz and C4. Negative potentials were observed in all the three conditions. Mirror mapping led to higher negativity compared to direct in central electrodes (paired t-test, p<0.001, Bonferroni corrected). Much weaker activity was found in the video condition. Negative deflections were also observed in fronto-central, central and parietal electrodes (FC, C, CP, P). Repeated measures ANOVA revealed a significant main effect of the conditions in 33 out of the 41 electrodes tested (p<0.05, Bonferroni corrected). The peak activity was reached within a window of approximately [0.8 1.05] sec from the time of the target onset (t=0). The negative SCPs were maximal in C1 electrode in the direct condition and equal to −7.22±0.26 μV (mean±standard error), in Cz electrode in the mirror condition (−11.02±0.28 μT) and in C2 in the video (−2.97±0.28 μV).

More interestingly, an activity shift towards electrodes ipsilateral to the moving hand was observed in the case of the mirror mapping. In FIG. 14 it is observed that the wave-forms of C3 and C4 are at more similar voltage levels in the mirror mapping compared to the direct. FIG. 15 depicts four measures of hemispheric laterality that were used, namely the differences between the SCPs peak negativity in four pairs of sagittally symmetric electrodes: C3-C4, CP3-CP4, FC3-FC4, FC1-FC2. The average difference between C3 and C4 SCPs peak values (FIG. 15a) was significantly smaller by absolute value for the mirror condition compared to direct (paired t-test, p<0.001), Similarly, with CP3-CP4 (FIG. 15b) smaller difference was observed in the mirror versus the direct condition (paired t-test, p<0.001). The same applies also to the FC3-FC4 pair (FIG. 15c) (paired t-test, p<0.001) and to FC1-FC2 (FIG. 15d) (paired t-test, p<0.01).

FIG. 16 depicts the scalp topographies of the SCPs peak negativity within the time-window [0.8 to 1.05] sec. The direct condition exhibits the lateralized activity towards the left hemisphere that was expected. Interestingly, in the case of the mirror mapping, even though the same hand is used to perform the task, there is a shift in the activity towards more central and ipsilateral locations. In the video observation of the left hand, one can observe some negativity towards the right hemisphere, as expected, but much weaker.

Figures 17A, 17B, 17C:
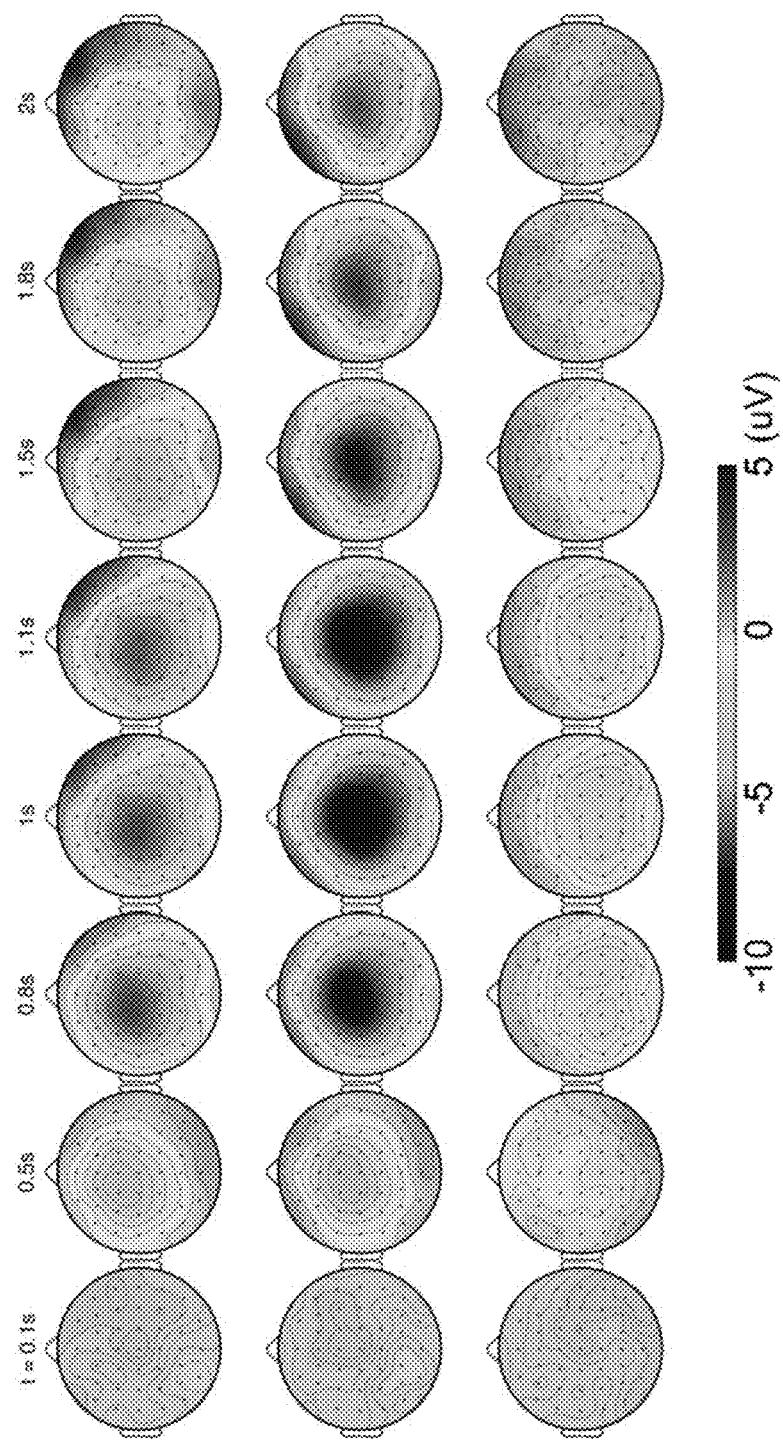
FIGS. 17A-17C show scalp topographic evolution of SCPs for the three conditions. From upper to lower row: direct (FIG. 17A), mirror (FIG. 17B), video (FIG. 17C). Stronger and less lateralized activity is progressively established in the mirror condition. The activity lasts longer, presumably reflecting the longer duration of the mirror task.

FIG. 17 shows the progression of the activity and the hemispheric shift in time, where the grand average SCPs are plotted in selected time-points, covering the first 2 seconds after the target onset, with higher density around the maximal activity. In t=0.5 sec after the target onset the activity is similar in the direct and the mirror conditions. After this point, progressively stronger and less lateralized activity is established in the mirror condition. Moreover, this activity lasts longer.

To further investigate this shift towards a hemispheric balanced activation, single-trial classification was performed. The obtained ROC curves of C3, C1, Cz, C2 and C3 electrodes can be seen in FIG. 18. The ROC curves of the 10 cross-validation folds are plotted in grey and the mean curve across the folds in blue. The line that corresponds to random performance is marked in red. The AUC is higher for Cz and C2 electrodes (FIGS. 18d and 18e), namely 0.65 0.04 (mean standard error). The performance of C3 electrode (FIG. 18b) is at the levels of random 0.51+/−0.04 and the performance of C4 (FIG. 18f) is close to Cz and C2 (0.63+/−0.04). The probability of random classification with our dataset is 0.54.

Figure 19:
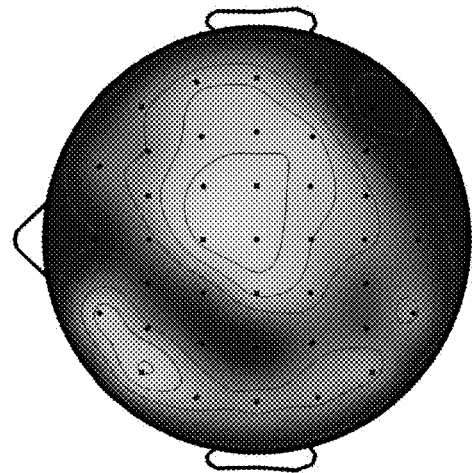
FIG. 19 illustrates an exemplary scalp topography of mean AUC of single-trial classification of direct vs. mirror in accordance with preferred embodiments. The discriminability is higher for central and ipsilateral electrodes.
Figure 20A:
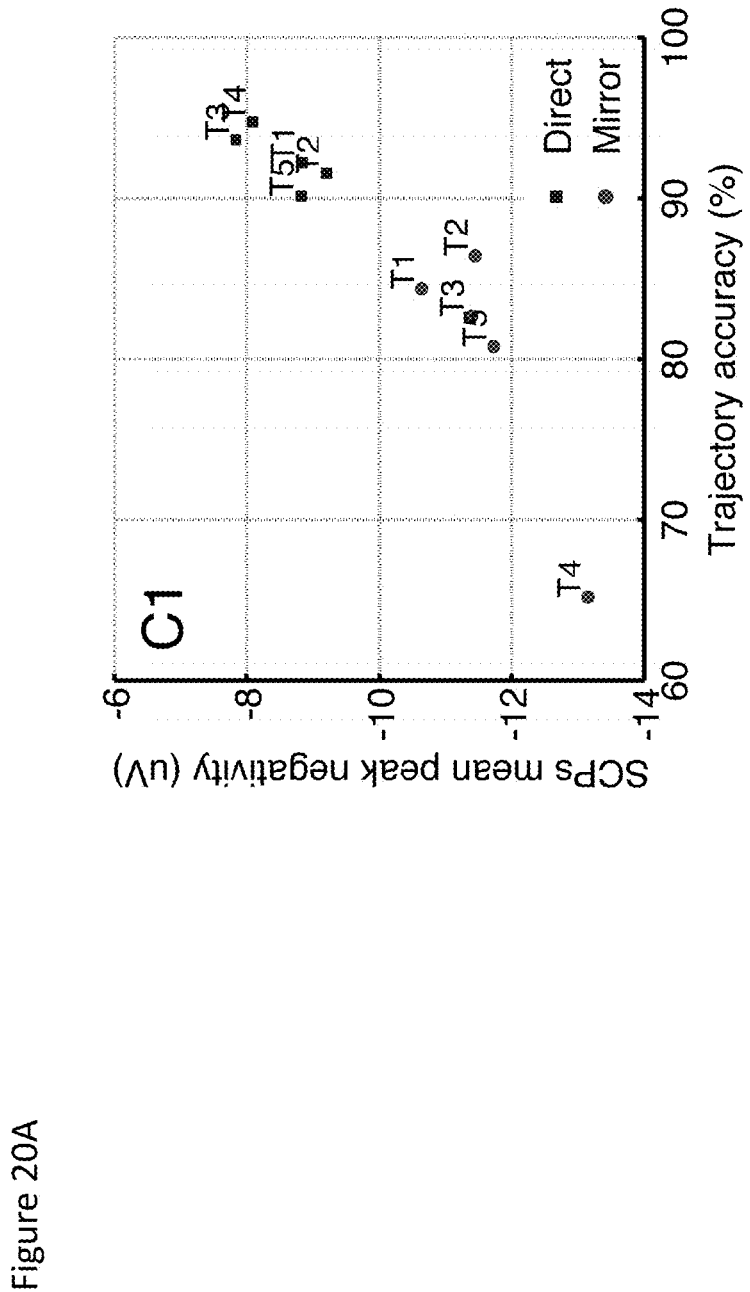
FIG. 20A illustrates mean SCPs peak negativity vs. mean trajectory accuracy for the 5 targets within each condition for C1 electrode according to preferred embodiments. Correlation was observed in the mirror condition where r=0.92 but not statistically significant (p-value>0.05).
Figure 20B:
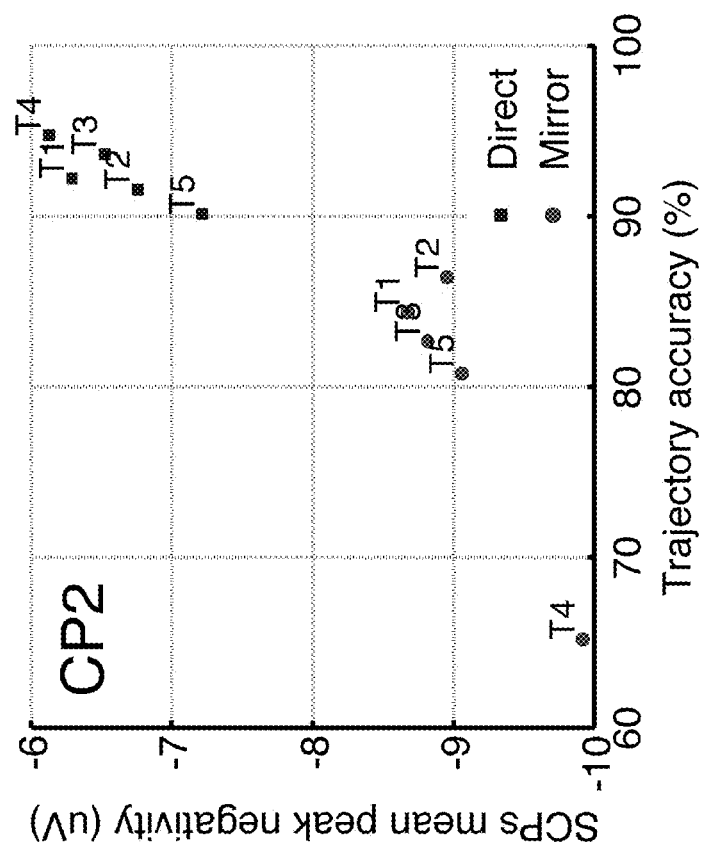
FIG. 20B illustrates mean SCPs peak negativity vs. mean trajectory accuracy for the 5 targets within each condition for CP2 electrode according to preferred embodiments. Correlation was observed in the mirror condition where r=0.95 but not statistically significant (p-value>0.05).

Plotting the mean AUC for all the electrodes topographically, the discriminability map shown in FIG. 19 was obtained. The ability to discriminate between direct and mirror mapping is higher for central and ipsilateral electrodes. This result provides further evidence for ipsilateral excitability and may suggest a possible ipsilateral source of activity.

Our analysis of SCPs suggests that mirrored visual feedback in a VR task can lead increased cortical excitability to the hemisphere ipsilateral to the hand in use. This finding provides neurophysiological insights to mirror therapy and is in line with existing literature (Fukumura et al., 2007; Garry et al., 2005; Kang et al., 2012; Touzalin-chretien and Dufour, 2008). Ipsilateral tissue facilitation may be one of the possible background mechanisms of mirror therapy. Such evidence can have important implications in the design of neurorehabilitation procedures and in maximally exploiting the potential of virtual reality manipulations in this context.

Example 3—VR Assessment and Treatment of Hemispatial Neglect

The tasks evaluated perception of near space and then perception of far space.

The setup was constructed according to FIG. 1B, featuring Oculus Rift DK2 and the camera of MindMaze that assures accurate motion tracking.

The 3D environment and CSV files scripts (C#) were made using Unity 5.2.0 f3 personal.

Statistics were generated from the CSV files to an Excel sheet using Python 2.7 scripts.

The participant is seated in front of a real table and the observer has to pay attention that this one is centered with the camera. Markers were attached to the patient as previously described.

Calibrations were then performed for correct placement of the subject and markers.

Then, the Oculus is put and adjusted on the participant's head. Depending on the eye characteristic of the participant, one can adjust the distance to the lenses of the Oculus, and the lenses themselves (set A of lens are for people with a quite good sight whereas set B is for participant with myopia).

Perception of Near Space

The goal of the first task was to evaluate the close (i.e. peri-personal) space. The task consists in reaching statics targets spread around reaching space. Three levels of difficulty were defined to increase the test sensitivity.

The following instructions were given to each participant:

Exercises will be done only using the right hand. You will see a succession of mug that will appear one by one at different location in your vision field. The task will be to touch the mug, when you will be above it will become yellow then green to finally disappear. Once the mug has disappeared you have to go back to the resting position represented by a blue circle (see FIG. 21).

In order to make the mug appear, you have to wait for the blue circle to become green and disappear.

Before starting a new level, a test is made to assure the participant understands well the instructions.

This test consists in taking 5 times a mug that appears at the same location on the right because if the participant has neglect he has to return to the previous level.

For level 1 (no distractors) we simply give the instruction written above.

For level 2 (distractors) we tell him that some elements in the space will be animated but he has to stay focused on taking the mug because no question will be asked concerning the other appearing elements.

For level 3 (dual task), we put the headphones on the participant's head and the following instructions are added:

You will hear two kinds of sounds, one is a bell and the other one is a hammer hitting a table. When you'll hear the bell, you'll have to tell me «yes». But at the same time you will have to take the mug as in the previous levels.

Before starting the level, we made a small auditory test with only the two sounds (touch «1» for the hammer, touch «2» for the bell) to be sure the participant distinguishes well the two sounds. Without wishing to be limited by a closed list, such different auditory stimuli represent a significant advantage over other types of tests, such as paper or electronic table-based tests, as they increase the sensitivity of the assessment.

Once the level is launched, the observer has to press on the space bar each time the participant says «yes» in order to count them.

Figure 21:
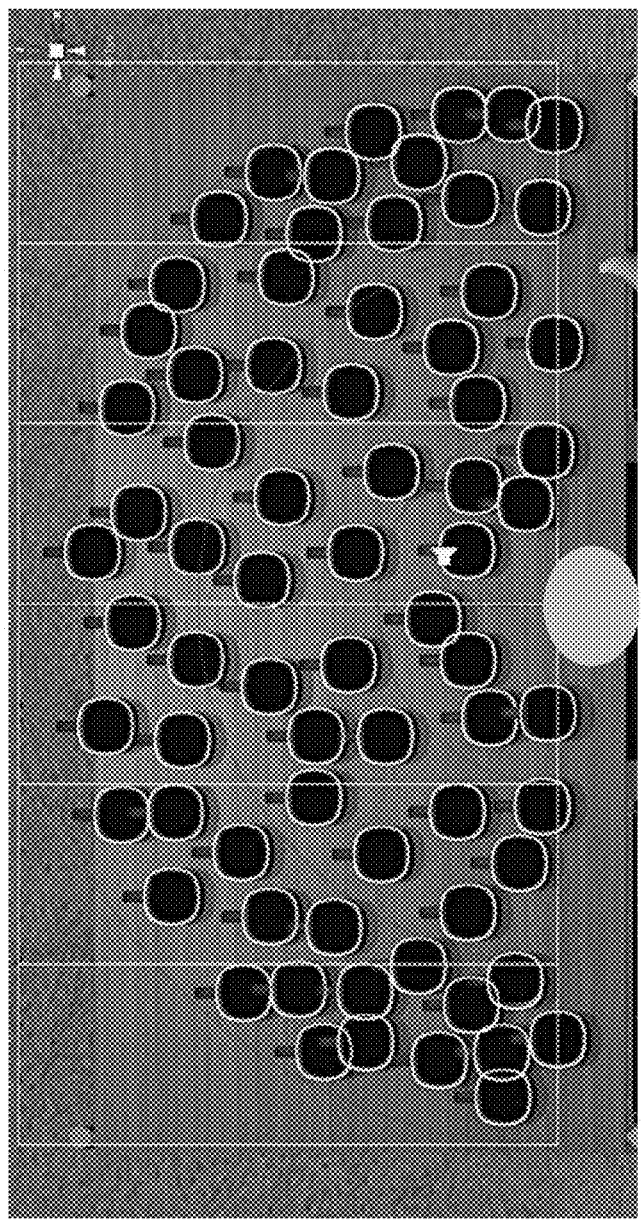
FIG. 21 illustrates exemplary mug distribution and starting position in blue in the close space task using Oculus Rift according to preferred embodiments.

Next, the peri-personal space was divided into six columns and three semi-circular areas as shown in FIG. 21. Each column contains 12 mugs and in each column, the area delimited by the column and circle intersection contained the same number of mugs. The scale of the frame is sized during the calibration steps (space command).

With this distribution, the near, mid and far peripheral vision are well evaluated because it is much more balanced according to the human eye and human vision.

To balance the distractors, we decided that each column would contain the following occurrences:

| | |
|---|---|
| 1 Left Lamp | 1 Left TV |
| 1 Right Lamp | 1 Right TV |
| 2 TV Screen | 1 TV Screen + Left Chrono |
| 1 Left Chrono | 1 TV Screen + Right Chrono |
| 1 Right Chrono | 1 TV Screen + Left Lamp |
| 1 TV Screen + Right Lamp | |

Here is the list of the collected parameters:

Omitted Target with their corresponding position and distractors. A target is said be omitted if it has not been touched after a duration of 2× average of reaching time for the trial Reaction time for each target. Time that the participant took to move the hand of 2 cm starting from the appearance of the target Reaching time for each target. Time between the appearance of the target and the moment the target disappears after being touched Total time of the exercise Average reaction and reaching time by column Average reaction and reaching time per side Standard deviation of reaction and reaching time per side Hand position (via wrist marker position).

Interpolation of left and right area covered by the hand and calculation of the relative area.

Time toward left and right direction (via head orientation data)

Total omitted targets

Ratio time: Exploration time on the right (or left)/number of targets cancelled on the right (or left).

Perception of Far Space

The goal of the task was to evaluate the far (i.e. extra-personal) space. The task consists of pointing to static targets spread around the extra-personal space, Four levels of difficulty were defined to increase the test sensitivity.

Figure 22:
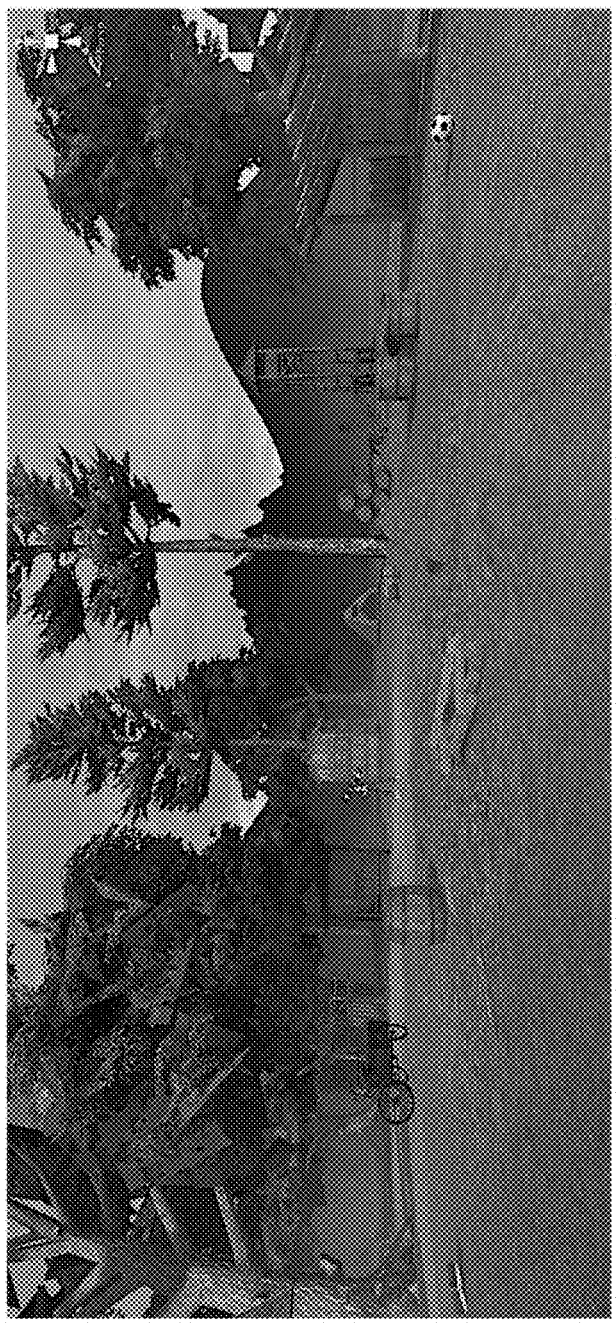
FIG. 22 illustrates an exemplary environment displayed to a participant via the Oculus Rift in the far space task according to preferred embodiments.

The setup and procedure was as previously described, but without the additional markers on the body of the subject. The subject is immersed in a forest composed of many objects as presented in FIG. 22. Before starting the first level, the participant makes a small training.

The observer gives the following corresponding instructions: «at the center of the screen you should see a red dot, if you move the head, the dot will move. You have to aim the blue box with the red dot by moving the head, once you are in the blue box you have press on the space bar and the color of the box will change. You have to do that for the 4 blue boxes».

The observer must ensure to put the right hand of the participant on the space bar because the participant cannot see it due to the Oculus system.

Before clicking on a given level, the instructor explains the task and should avoid speaking with the participant while he is doing the level.

For level 1 the observer gives the following instructions:
You will see many objects on the environment; you have to aim everything except the plants, tree and fire. As the training, you have to press on the space bar once you are on the objects. When you have finished tell me and I will stop the level.

For level 2 we add to the environment some moving targets that are rabbit either alone or by group of 2. The Observer gives the participant the followings explanations:
You will see some moving targets that are rabbits; the purpose is to aim it using the light spot that will be projected on the ground. Once you have put the spot on the rabbit by moving the head you have to press on the space bar, if you aim correctly the rabbits the light spot will be blue. It is important that you see the blue color because the reaction time is saved once the color has changed. If you don't observe it, press on the space bar until it becomes blue.

You can press once even if there are 2 rabbits.

Figure 23:
FIG. 23 illustrates that the boar and chicken are the two distractors, and the rabbit on the right is the target, in the far space task according to preferred embodiments.

For level 3 we add some distractors to the environment in order to test potential attention deficit in a participant. The distractors are big (boar) or smaller (chicken) and appear by group of 2 or alone. FIG. 23 shows an example.

The observer tells the participant that he will see multiple animals, but he has to aim at the rabbits, and only the rabbits.

Before starting the level 4 we provide two sounds to the participant, one is a barking dog and the other is a cricket. We next tell him that he will have to say «yes» each time he hears a dog, but he has to aim at the rabbits and only the rabbits similarly to level 3.

Figure 24:
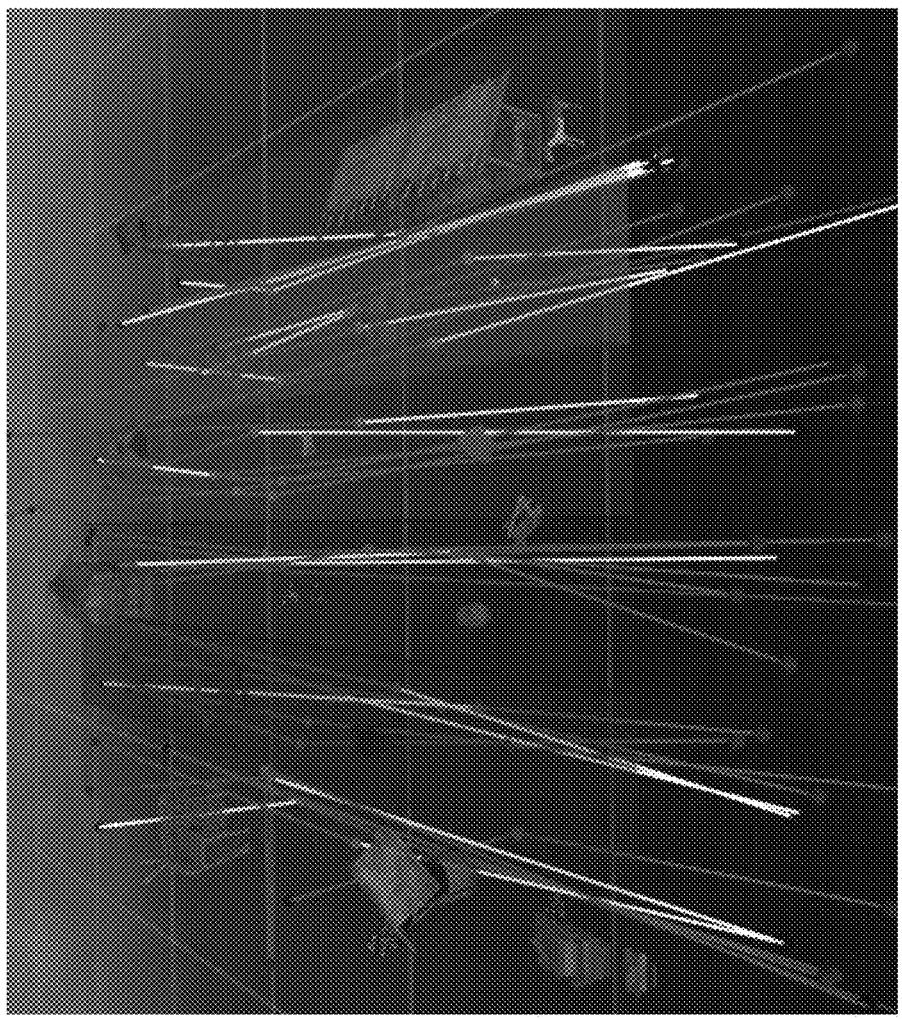
FIG. 24 illustrates tracers showing the path taken by the rabbits with 50% of them coming from the top and the others from the bottom of the VR visual field according to preferred embodiments.

The space is divided in six columns (L3-L2-L1-R1-R2-R3) and six sequences of apparition of rabbits and distractors (level 3 and 4) are set in each column as shown in FIG. 24.

Almost 50% sequences of apparition (10) with boar are on the and on the right (9), same for chicken (8 left, 9 right).

Moreover, we could choose the whole pathway of targets and distractors. So 50% of distractors and targets come from the bottom of the scene and 50% from the top. We choose that the animals will appear either alone either by group of 2 in a balanced way. We have taken one kind of small distractors (chicken) and one kind of big distractors (boar) as shown FIG. 23 to see if the size has an effect on the way they distract the participants.

We have been particularly focused on the order of animal apparitions because we wanted to make move the head of the participant from left to right to avoid that the participant memorizes a kind of repetitive sequence of apparition.

In order to do that, we chose the following design:
Try to avoid displaying the same kind of distractors consecutively
Didn't display rabbits in the same column consecutively
If a rabbit come from the top of one column, we didn't display the following rabbits on the bottom of the neighboring column, else it would be to easy for the participant.
Try to avoid displaying rabbits on the same side consecutively (in more than 60% of the times the subject had to cross the central line in order to see the targets on the other side).

Since we wanted to see the effect of distractors on the participant, we have judged that we shouldn't put both distractors and targets in the top right or bottom right, same for the left side. For example, if a rabbit and a distractor are on the bottom left, the participants will see both at the same time and the distractors will have not distracted the participants.

Since we have 18 left distractors and right distractors, their apparition locations are as follow:
If the rabbits appear on the bottom left, we will have 6 times a distractor on the top left and 12 times a distractor on the right.
If the rabbits appear on the top of the left, we will have 6 times a distractor on the bottom left, 6 times a distractor on the bottom right and 6 times a distractor on the top of right
If the rabbits appear on the bottom right, we will have 6 times a distractor on the top right, 6 times a distractor on the bottom left and 6 times a distractor on the top of the left
If the rabbits appear on the top of the right, we will have 6 times a distractor on the bottom right, 6 times a distractor on the bottom left and 6 times a distractor on the top of the left.

Here is the list the collected parameters:
Omitted Target with their corresponding position and distractors. A target is said omitted if it has not been touched after a duration of 2× average of reaching time for the trial
Reaching time for each target
Time required to aim correctly at a target, that is to say when the light spot changes his color from yellow to blue
Total time of the exercise
Total average marking distance: total average distance between two consecutive cancelled objects (level 1)
Left and right marking distance: average distance to go from one object to the following one on the left or the right (level 1)
Total standard deviation of marking distance, and also for left and right side (level 1)
Total average marking time: total average time taken between two consecutive cancelled objects (level 1)
Total standard deviation of marking time, and also for left and right side (level 1)
Left and right marking time: average time to go from one object to the following one on the left or the right (level 1)
Average reaching time by column: Average time required to aim correctly a target in a given column, that is to say the time between the appearance of the animal to the change of light color of spot
Average reaching time per side: Average time required to aim correctly a target for each side, that is to say the time between the appearance of the animal to the change of light color of spot
Standard deviation of reaching time per side
Time toward left and right direction (via head orientation data)
Total omitted targets
Ratio time: Exploration time on the right (or left)/number of targets cancelled on the right (or left)
Number and Kind of Distractors Cancelled by Mistake Experimental Validation Upon arrival, the participants read and signed the consent form. They performed the Edinburgh Test for handedness. The order of the tasks was pseudo-randomized across participants.

Results—VR-Based Assessment of Close Space

We conducted a study with 37 right-handed healthy participants (average age: 49.72 years, range 39-70, 14 women and 23 men) to evaluate the close tasks.

Figure 25:
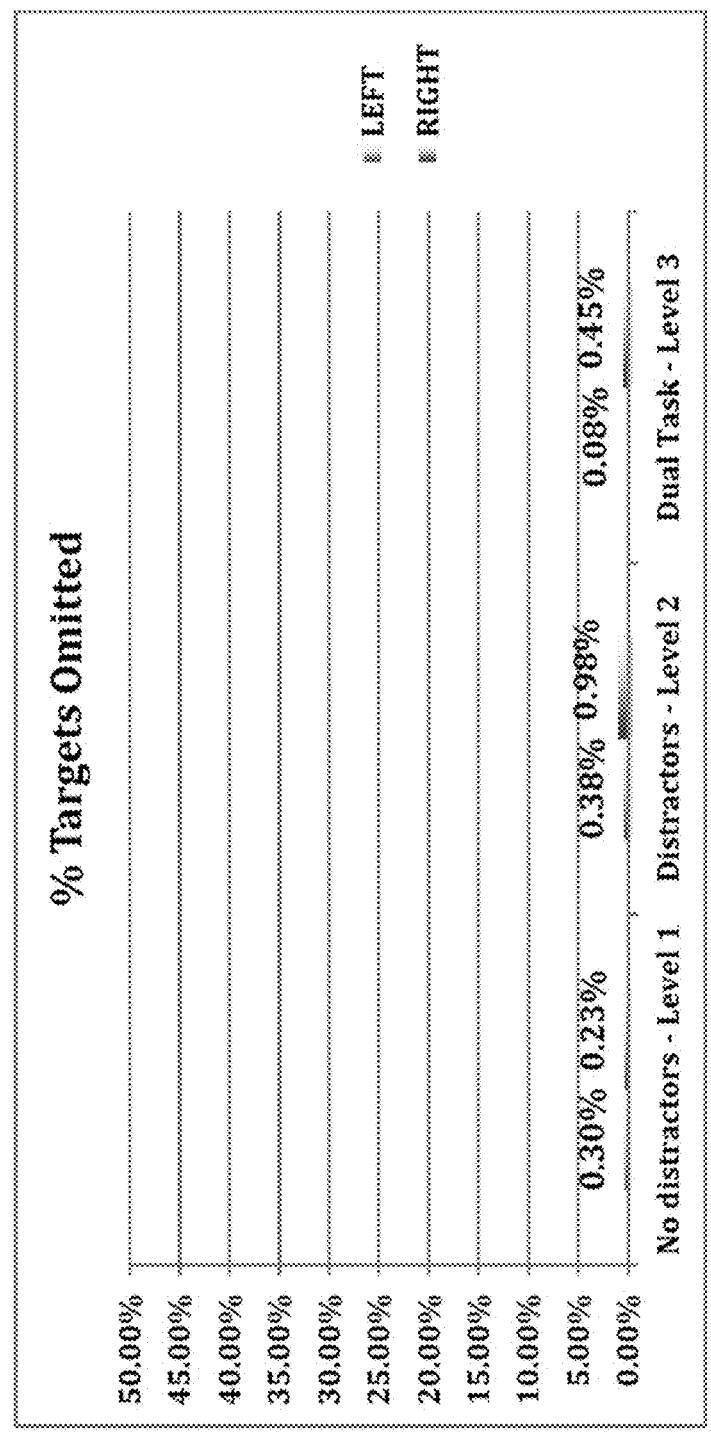
FIG. 25 illustrates a chart showing the percentage of omitted mugs in left and right side in the close space task using Oculus Rift according to preferred embodiments.

The main results and findings are shown in the following figures and described as follows. We can observe in FIG. 25 that the task is well designed since difference between left and right results is not significant so both side are balanced. Furthermore, healthy participants missed very few targets so the task is by far not difficult and could be used for patients.

Figure 26:
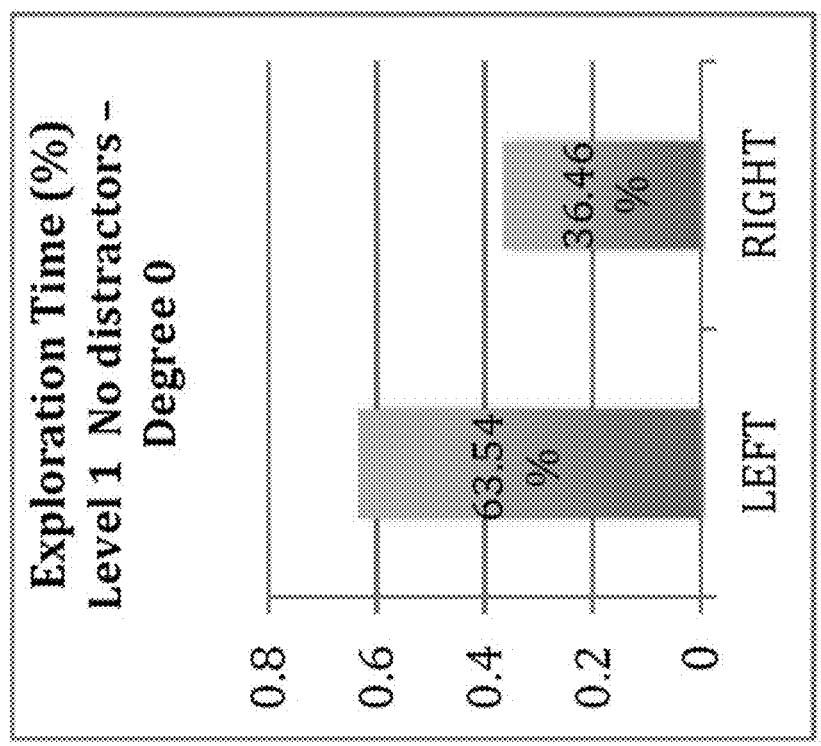
FIG. 26 illustrates a chart showing exploration time in left and right side based on head motion tracking according to preferred embodiments.
Figure 27:
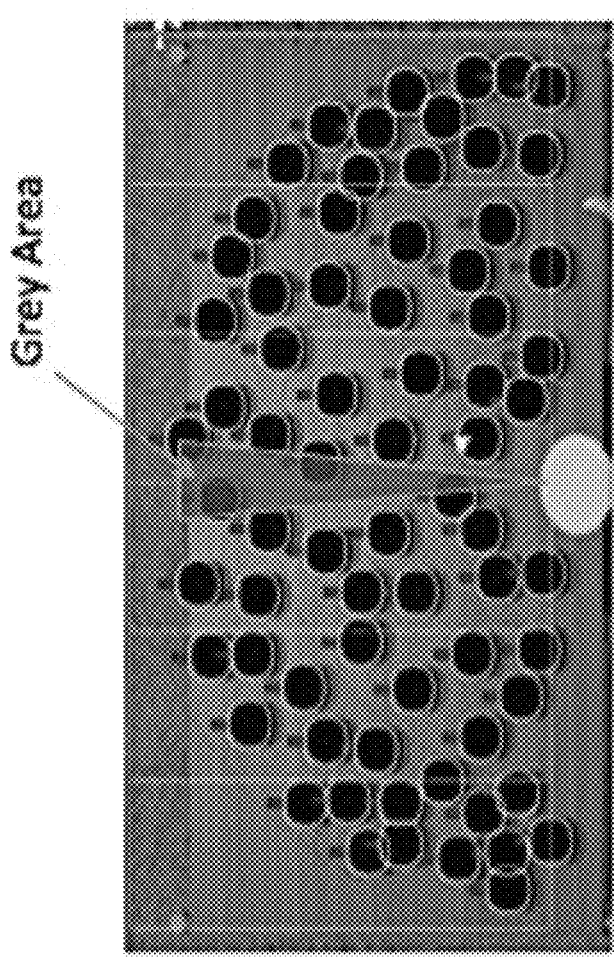
FIG. 27 illustrates exemplary mug distribution showing a grey area covering an angle from 0 to 5 degrees with respect to the bisector of this area according to preferred embodiments.

The results displayed in FIG. 26 show that the exploration time distribution is not balanced (we expected to have equal exploration time in both sides). We suspect that participants may be using mainly the eyes (and not head) to search for the objects in the space. Therefore, a grey area was added in the center of the scene as shown in FIG. 27. Mugs that are in this area are neither considered to the right nor to the left.

In order to find what is the participants' strategy of observation, i.e. either by moving the head or by moving the eyes, we have changed the angle of this grey area from 0 to 5° (counting from Pi/2 so the opening angle is 0, 2, 4 or 10°).

Figure 28:
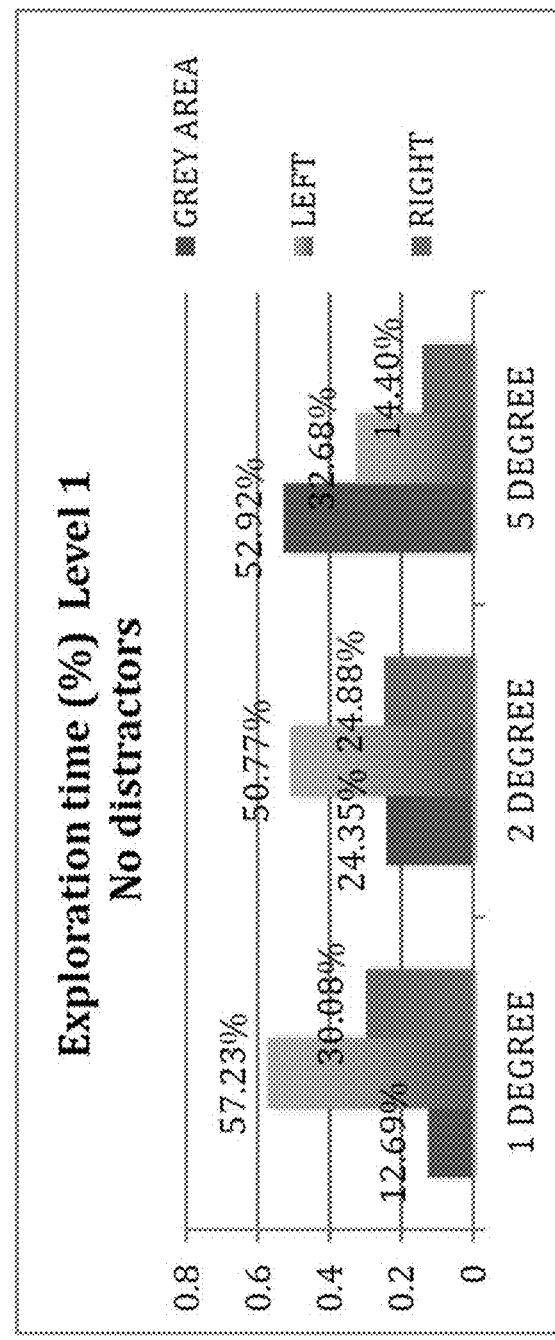
FIG. 28 illustrates a chart showing time of exploration in the left, right and grey (central) area depending on the opening angle in accordance with preferred embodiments.

FIG. 28 clearly shows that a very small angle change has a strong impact on the exploration time distribution since we have more than 50% of the time spent on the grey area when the opening angle is only 10°. Thus the conclusion is that participants mainly move their eyes to do that task. An optional addition would be to include an eye tracking system in the HMD.

It is possible to use data related to head motion but we can also process data coming from wrist markers position in order to see how participants explore the space with their hand. In order to do that we have made an algorithm which find the approximate resting position center (in red) in that way we can find the centerline of the scene to next plot the convex hull of the wrist position on each side and finally compute relative area covered by left and fight hand.

Figure 29:
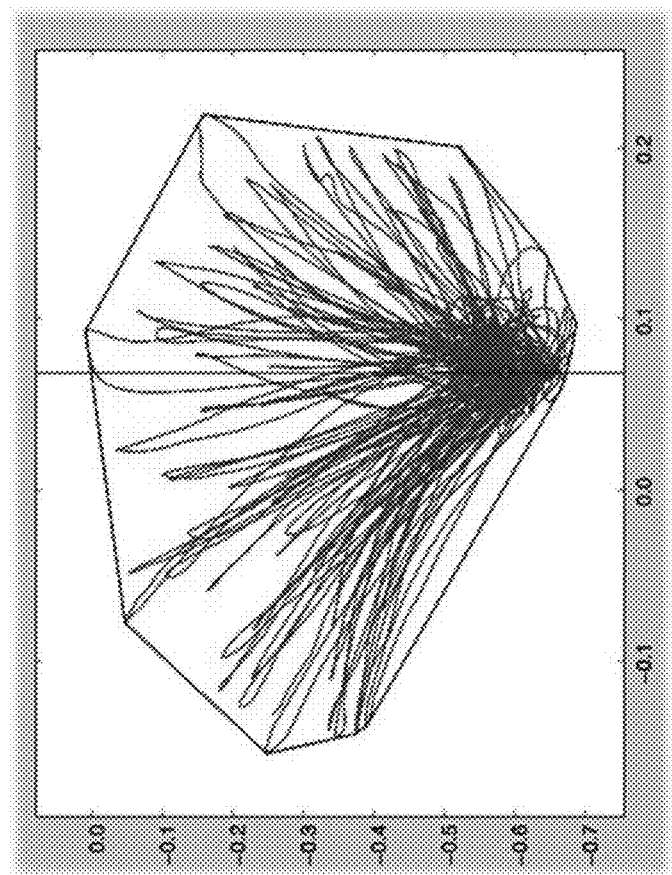
FIG. 29 illustrates a chart of exemplary trajectories covered by the right hand of a participant according to preferred embodiments. Trajectories are based on marker at the wrist; red dot represent the approximate resting position.

FIG. 29 shows trajectories done by the right hand in both side and the resulting convex hull of such trajectories. We can see that space exploration by the hand is not fully balanced as expected; this result can be strongly improved by simply put marker on the hand or finger instead of the wrist because when the marker is put on the wrist, the hand rotation is not taken into account.

Results—VR-Based Assessment of Far Space

We conducted a study with 39 right-handed healthy participants (average age: 49.43 years, range 39-70, 16 women and 23 men).

Figure 30:
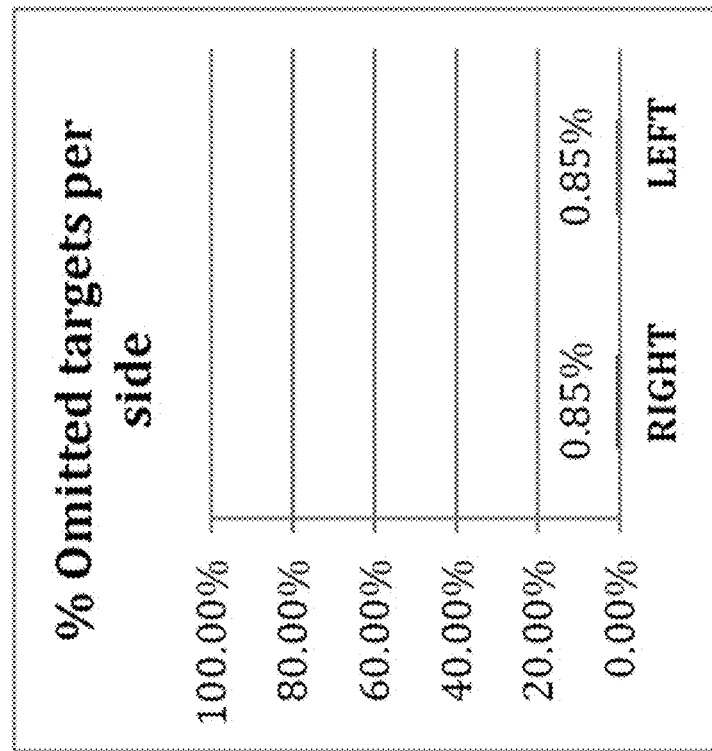
FIG. 30 illustrates a chart showing the percentage of omitted static targets (Level 1) in right and left side according to preferred embodiments.
Figure 31:
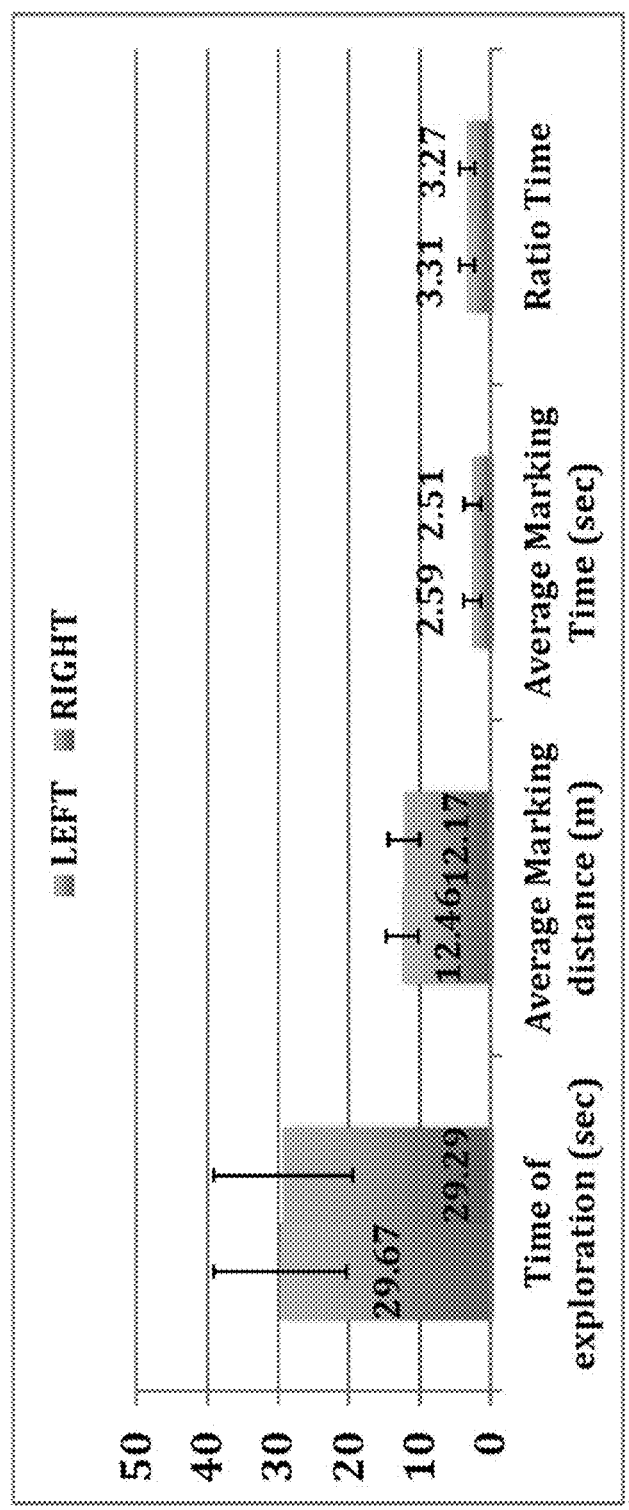
FIG. 31 illustrates a chart showing an example of new parameters for Level 1 according to preferred embodiments.

The task is well designed for level 1 since the number of omitted targets is equal in both sides as shown in FIG. 30. Some new parameters have been added to make the level more sensitive. Based on the results in FIG. 31, we can see that all the new parameters are almost balanced, thus we can potentially rely on them to assess hemi-spatial neglect.

Figure 32:
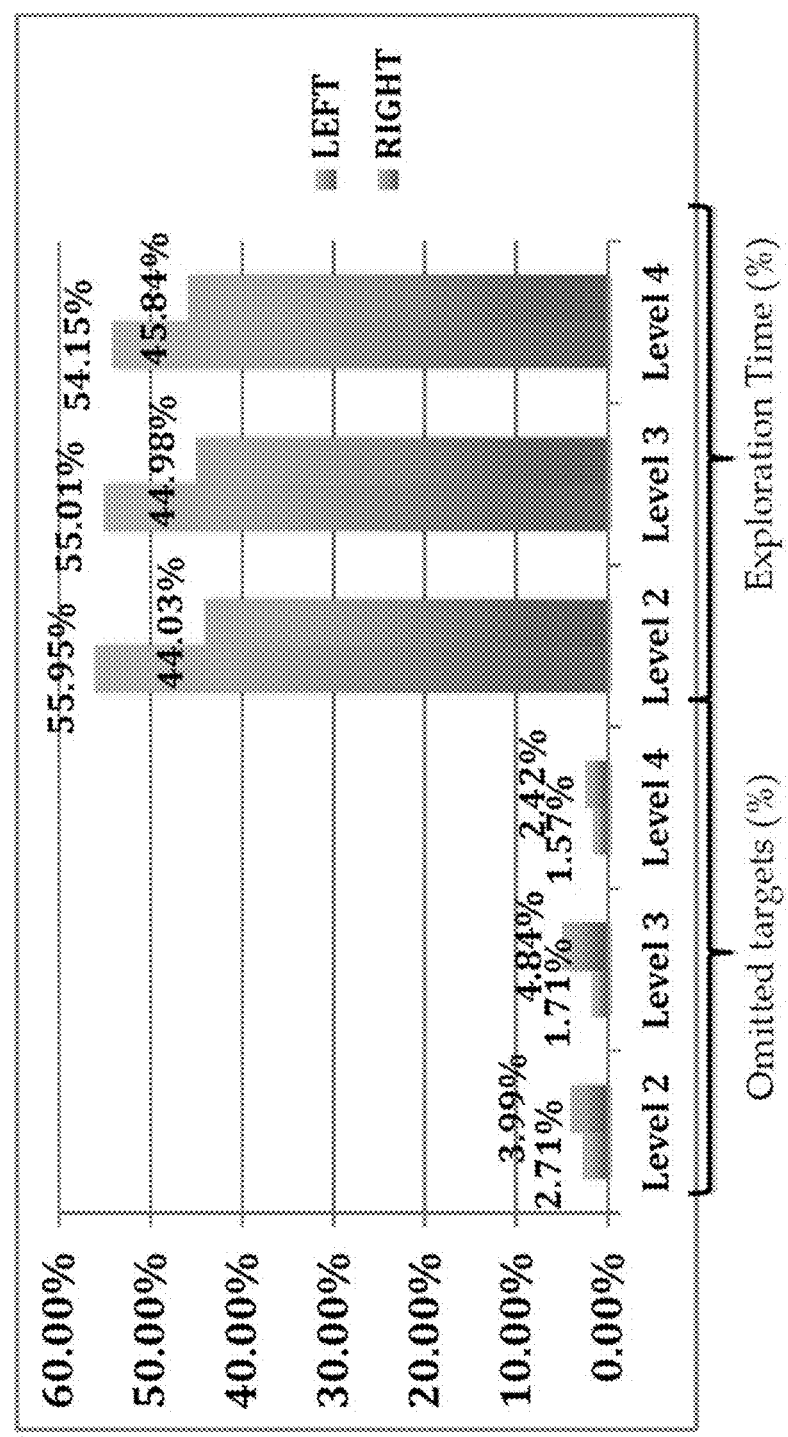
FIG. 32 illustrates a chart showing the percentage of omitted rabbits and exploration time for both sides and levels 2, 3, 4 according to preferred embodiments.

FIG. 32 shows that there is a slightly higher number of omitted targets on the right compared to the left side. A direct correlation with the exploration time can be made since we have a bit lower of exploration time spent on the right compared to the left. The hypothesis is that we put a kind of cowshed on the extreme right so the depth of the landscape is a bit broken compared to left side that is more opened. The possible consequence is that participant will look preferentially on the side that offers a more open environment. Thus, those two parameters can be improved by studying more the impact of size and location of object on the way people explore a scene.

As shown FIG. 32, the time exploration based on head motion is a good parameter in the far space.

Figures 33A, 33B:
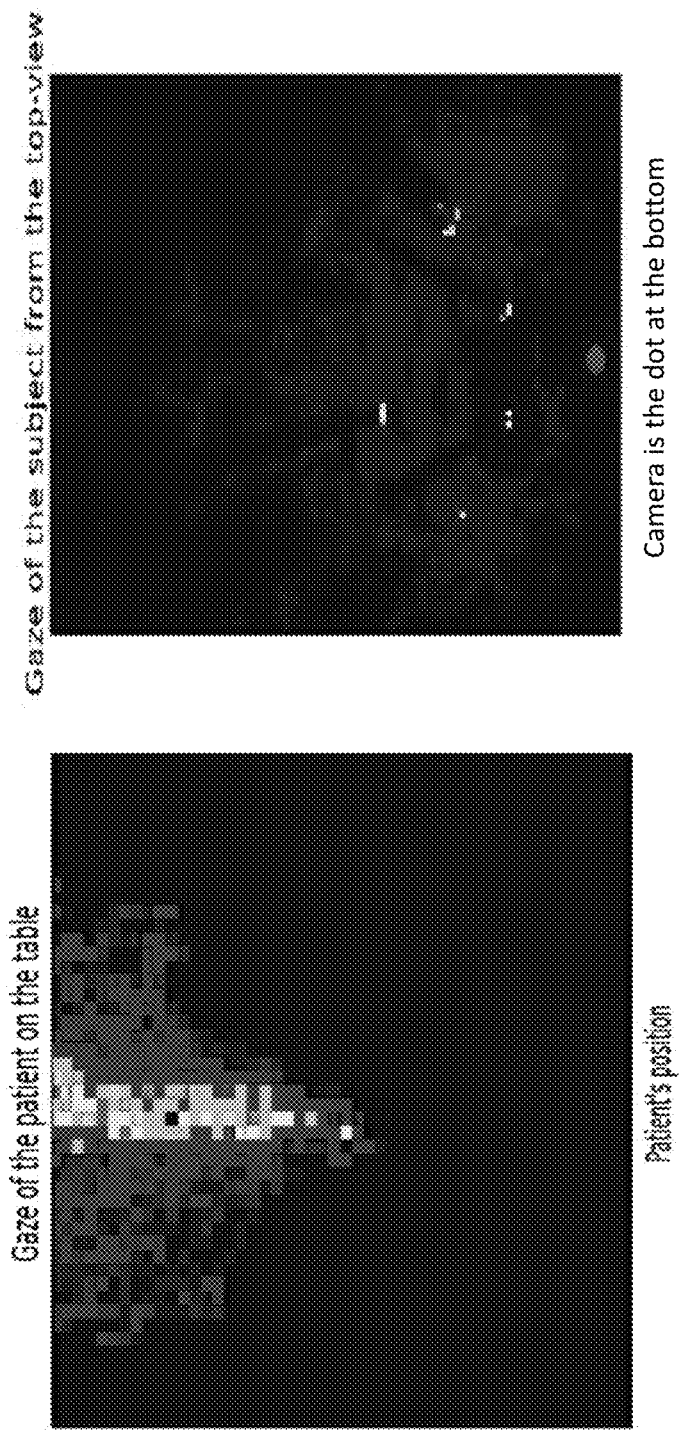
FIGS. 33A-33B illustrate a chart showing the head gaze map of a participant (C17) for a dual-task close space and dual-task far space according to preferred embodiments.

FIG. 33 opposes gaze map of dual-task of close and far space task for one participant. We can clearly see that far space tasks makes the head of the participant moves way more than close space tasks where points are mainly in the central area (=grey area).

These tests demonstrate that the tasks evaluate peri- and extra-personal space, which consequently make such assessments more powerful compared to standards tests.

Different levels of difficulty and large sets of parameters have been computed, thus leading to more sensitive tests, with more than 35 new parameters compared to classic paper-pencil tests.

VR offers endless opportunities to analyze subject behavior in multiple ecological and controlled situations. Using such technology, we can easily test the sensitivity of the new parameters in order to give the best diagnostic for each patient.

This will finally lead to more effective and customized rehabilitation where each patient will train his brain by playing with playful and entertaining games where vision and auditory ability are challenged.

Example 1—Verification of Patient Diagnosis in an IVR (Immersive VR) Environment Methods: 12 chronic stroke patients (58±9.4 years; 5 female; time from stroke: 15.8±7.7 months) completed a battery of paper-and-pencil neuropsychological tests (bisection, cancellation, reading, drawing, functional scales) and a IVR-based assessment for extra-personal USN (unilateral spatial neglect). In the IVR tasks, participants were presented with a virtual forest environment via head-mounted display (Oculus DK2). The 4-level task consisted of finding static objects (level 1) or moving rabbits (levels 2-4) in the scene, with or without the presence of distractors and an additional auditory dual task to induce a cognitive overload. Participants used the embedded head tracker in the 1-MD (head mounted display) to control a pointer to select the targets in the scene, and the space bar of the computer to validate the selected item.

Results: Four patients presented USN in both paper-and-pencil and IVR tasks. Interestingly, two other participants showed signs of neglect in the IVR assessment but were not classified as neglect in the paper-and-pencil tests. These patients did not show any sign of USN in the items of the Catherine Bergego Scale that assesses their ability to explore the extra-personal space.

This preliminary data suggests that IVR-based assessments represent an easy-to-use and consistent tool to investigate USN, can extend its evaluation to the far space, and can detect USN in chronic patients who do not show sign of neglect in standard assessments.

While the invention has been described with respect to a limited number of embodiments, it will be appreciated that many variations, modifications and other applications of the invention may be made, including different combinations of various embodiments and sub-embodiments, even if not specifically described herein.

What is claimed is:

1. A method for assessing a patient suffering from spatial attention deficit with a computationally directed set of movements, the set of movements being directed by a computational system that comprises providing visual direction to the patient and tracking the movements of the patient, the computational system comprising a display, at least one tracking sensor and a plurality of machine instructions for controlling the display to provide the visual direction and for receiving sensor data from the tracking sensor to track the movements of the patient, the method comprising:

displaying a plurality of virtual objects to the patient, distributed according to a function of the spatial attention deficit;

indicating a movement to be performed by the patient with the virtual object;

tracking said movement using the computational system, the tracking comprising obtaining tracking data with said tracking sensor, obtaining tracking data with at least one inertial sensors attached to the patient and an inertial sensor receiver of the computational system, or both; analyzing the tracking data using a tracking engine to identify movements of the patient and generate patient movement data;

analyzing patient movement data using a data analysis layer to generate a display adjustment parameter and indicator adjustment parameter; and adjusting said displaying according to the display adjustment parameter and said indicating according to the indicator adjustment parameter, and according to a reaction of the patient to said plurality of virtual objects as determined according to said tracking;

wherein the patient is assessed according to said displaying, indicating and tracking.

2. The method of claim 1, further comprising:

analyzing a tracked movement, using a data analysis engine;

generating an indicator that identifies the movement to be perform wherein the tracking is performed with a depth camera and an RGB camera and a tracking engine and the adjusting the displaying and indicating the computational system comprises:

a depth camera and an RGB camera for obtaining tracking data, a tracking engine for tracking the movements of the patient, and a data analysis layer for analyzing the tracked movements and for adjusting said displaying and said indicating according to said tracking.

3. The method of claim 1, further comprising a virtual reality headset.

4. The method of claim 1, further comprising treating the patient according to said displaying, indicating and tracking.

5. The method of claim 4, wherein said displaying, indicating and tracking provides a higher degree of therapeutic intensity as compared to an intensive standard of care rehabilitative measure.

6. The method of claim 1, wherein the spatial attention deficit comprises hemi-spatial neglect.

7. A method for treating a patient suffering from hemispatial neglect with a computationally directed set of movements, the set of movements being directed by a computational system that comprises providing visual direction to the patient and tracking the movements of the patient, the method comprising:

displaying a plurality of virtual objects to the patient, distributed according to a function of the neglect;

indicating a movement to be performed by the patient with the virtual object;

tracking said movement; and adjusting said displaying and said indicating according to said tracking, and according to a reaction of the patient to said plurality of virtual objects;

wherein said displaying, indicating and tracking provides a higher degree of therapeutic intensity as compared to an intensive standard of care rehabilitative measure; and said higher degree of therapeutic intensity comprises increasing an amount of time the patient spends during each therapeutic session, increasing a number of exercises that the patient performs during said session within a specific time frame, or both.

8. The method of claim 7, further comprising providing an improvement from baseline in functional independence measured by the Bellmann test, star cancellation task, line bisection task, drawing tasks from a model, or drawing task from memory as compared to said standard of care rehabilitative measure.

9. The method of claim 7, further comprising providing an improvement from baseline in the general health status as measured by the Stroke Impact scale (SIS) as compared to said standard of care rehabilitative measure.

10. The method of claim 7, further comprising providing an improvement from baseline in the severity of stroke symptoms as measured by the NIH stroke scale (NIHSS) as compared to said standard of care rehabilitative measure.

11. The method of claim 7, further comprising providing an improvement from baseline in arm function in daily activities as measured by the Motor Activity Log (MAL) as compared to said standard of care rehabilitative measure.

12. The method of claim 7, further comprising providing an improvement in motivation measured by the Intrinsic Motivation Index (IMI) as compared to said standard of care rehabilitative measure.

13. The method of claim 7, further comprising reduced therapist time spent administrating rehabilitation exercises as compared to said standard of care rehabilitative measure.

14. The method of claim 7, further comprising providing an increased rehabilitation dose as measured by the duration of the rehabilitation session without planned rest periods as compared to said standard of care rehabilitative measure.

15. The method of claim 7, comprising performing the method during an acute period following a neurological trauma.

16. The method of claim 15, wherein said neurological trauma comprises one or more of stroke or head injury.

17. The method of claim 7, wherein the virtual object is displayed to the patient in an AR (augmented reality) or VR (virtual reality) environment.

18. The method of claim 7, further comprising measuring EEG signals of the patient during said tracking said movement by the patient.

19. The method of claim 18, further comprising providing feedback to the patient according to said EEG signals.

20. The method of claim 7, further comprising providing feedback to the patient through a visual display of a mirror avatar.

21. The method of claim 7, wherein the computational system comprises:

at least one inertial sensors attached to the patient and an inertial sensor receiver for obtaining tracking data, a tracking engine for tracking the movements of the patient, and a data analysis layer for analyzing the tracked movements and for adjusting said displaying and said indicating according to said tracking.

22. A method for rehabilitating a patient with a computationally directed set of movements, the set of movements being directed by a computational system that comprises providing visual direction to the patient and tracking the movements of the patient, the patient suffering from hemispheric neglect, the method comprising:

displaying a plurality of virtual objects to the patient through a VR or AR environment;

indicating a movement to be performed by the patient with the virtual objects;

tracking said movement; and adjusting said displaying and said indicating according to said tracking;

wherein the computational system comprises a depth camera and an RGB camera for obtaining tracking data, a tracking engine for tracking the movements of the patient, and a data analysis layer for analyzing the tracked movements and for adjusting said displaying and said indicating according to said tracking.

23. A method for assessing a patient with a computationally directed set of movements, the set of movements being directed by a computational system that comprises providing visual direction to the patient and tracking the movements of the patient, the patient suffering from hemispheric neglect, the method comprising:

displaying a plurality of virtual objects to the patient through a VR or AR environment;

indicating a movement to be performed by the patient with the virtual objects;

tracking said movement;

adjusting said displaying and said indicating according to said tracking; and assessing the patient according to said displaying, indicating and tracking;

wherein the computational system comprises a depth camera and an RGB camera for obtaining tracking data, a tracking engine for tracking the movements of the patient, and a data analysis layer for analyzing the tracked movements and for adjusting said displaying and said indicating according to said tracking.

24. The method of claim 23, further comprising treating the patient according to said displaying, indicating and tracking.

* * * * *